United States Patent
Koblanski

(10) Patent No.: US 8,116,858 B2
(45) Date of Patent: *Feb. 14, 2012

(54) METHODS AND APPARATUS FOR MONITORING HEART MOTIONS

(76) Inventor: John Koblanski, Vancouver (CA)

( * ) Notice: Subject to any disclaimer, the term of this patent is extended or adjusted under 35 U.S.C. 154(b) by 380 days.

This patent is subject to a terminal disclaimer.

(21) Appl. No.: 11/380,409

(22) Filed: Apr. 26, 2006

(65) Prior Publication Data

US 2007/0049848 A1 Mar. 1, 2007

Related U.S. Application Data

(63) Continuation-in-part of application No. 11/207,704, filed on Aug. 22, 2005, now Pat. No. 7,503,898.

(51) Int. Cl.
*A61B 5/02* (2006.01)
(52) U.S. Cl. ......... 600/513; 600/527; 600/587; 600/595
(58) Field of Classification Search .................. 600/513, 600/527, 587, 595
See application file for complete search history.

(56) References Cited

U.S. PATENT DOCUMENTS

| | | | |
|---|---|---|---|
| 3,593,703 A | | 7/1971 | Gunn et al. |
| 3,903,873 A | * | 9/1975 | Royal et al. ..................... 600/502 |
| 3,926,179 A | * | 12/1975 | Petzke et al. .................. 600/485 |
| 4,383,534 A | | 5/1983 | Peters |
| 4,530,354 A | | 7/1985 | Froilan |
| 4,967,759 A | | 11/1990 | Teves |
| 4,993,420 A | | 2/1991 | Welkowitz et al. |
| 5,033,472 A | | 7/1991 | Sato et al. |
| 5,080,107 A | | 1/1992 | Teves |
| 5,263,478 A | | 11/1993 | Davis |
| 5,293,874 A | | 3/1994 | Takahashi et al. |
| 5,345,632 A | * | 9/1994 | Langenaeken et al. ........... 5/601 |
| 5,445,144 A | | 8/1995 | Wodicka et al. |
| 5,865,759 A | | 2/1999 | Koblanski |
| 5,964,223 A | | 10/1999 | Baran |
| 6,171,258 B1 | | 1/2001 | Karakasoglu et al. |
| 6,292,689 B1 | | 9/2001 | Wallace et al. |
| 6,493,568 B1 | * | 12/2002 | Bell et al. ...................... 600/323 |
| 6,517,492 B2 | * | 2/2003 | Koblanski ..................... 600/481 |
| 6,681,423 B2 | * | 1/2004 | Zachrisson ....................... 5/610 |

(Continued)

FOREIGN PATENT DOCUMENTS

EP 0357275 A1 3/1990

(Continued)

OTHER PUBLICATIONS

Robert F. Rushmer, "Cardiovascular Dynamics," 1961, pp. 50-52, 91-97.

(Continued)

*Primary Examiner* — Kennedy Schaetzle
(74) *Attorney, Agent, or Firm* — Oyen Wiggs Green & Mutala LLP

(57) ABSTRACT

Methods and apparatus for monitoring the heart motion of a subject employ a probe which can be coupled to a portion of the anatomy of a subject such as the aortic arch or the thyroid cartilage. The probe is biased into contact with the subject. The probe detects movements caused by the heart motion. The apparatus may display accelerations and displacements caused by the heart motion. Waveforms from multiple anatomic sites may be acquired, normalized in time and amplitude, and combined to produce resultant waveforms. Combining the waveforms may involve addition or subtraction.

46 Claims, 17 Drawing Sheets

U.S. PATENT DOCUMENTS 6,726,635 B1 * 4/2004 LaSala .......................... 600/528
2005/0154285 A1 7/2005 Neason

FOREIGN PATENT DOCUMENTS

| EP | 0444594 A1 | 9/1991 |
| EP | 0764842 A2 | 3/1997 |
| FR | 2672794 A1 | 8/1992 |

OTHER PUBLICATIONS

Robert F. Rushmer, "Initial Ventricular Impulse APotential Key to Cardiac Evaluation" Circulation—vol. 29, 1964, pp. 268-283.

Alberto Benchimol, "Ultrasound," Textbook: Non-Invasive Diagnostic Techniques in Cardiology, 1977, pp. 15-38.

XP-002072289, Tavel, "Clinical Phonocardiography and External Pulse Recording", Year Book Medical Publishers, Inc., 1978.

Tavel, "Normal Sounds and Pulses: Relationships and Intervals Between the Various Events", Clinical Phonocardiography and External Pulse Recording, 4th Edition, 1978, pp. 39-45.

Tavel, "Ejection Sound (Ejection Click)", Clinical Phonocardiography and External Pulse Recording, 3rd Edition, 1978, pp. 75-78.

* cited by examiner

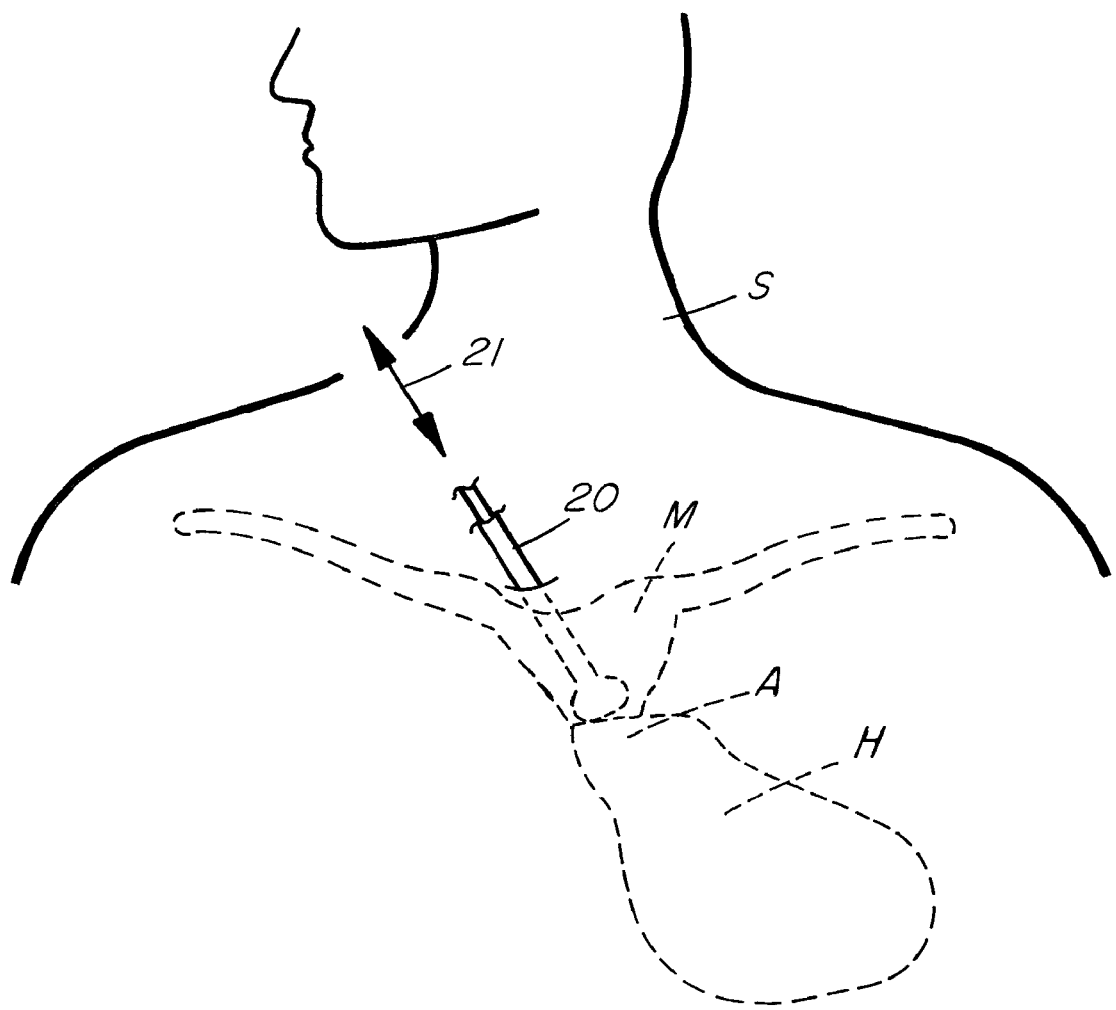
FIG. IA

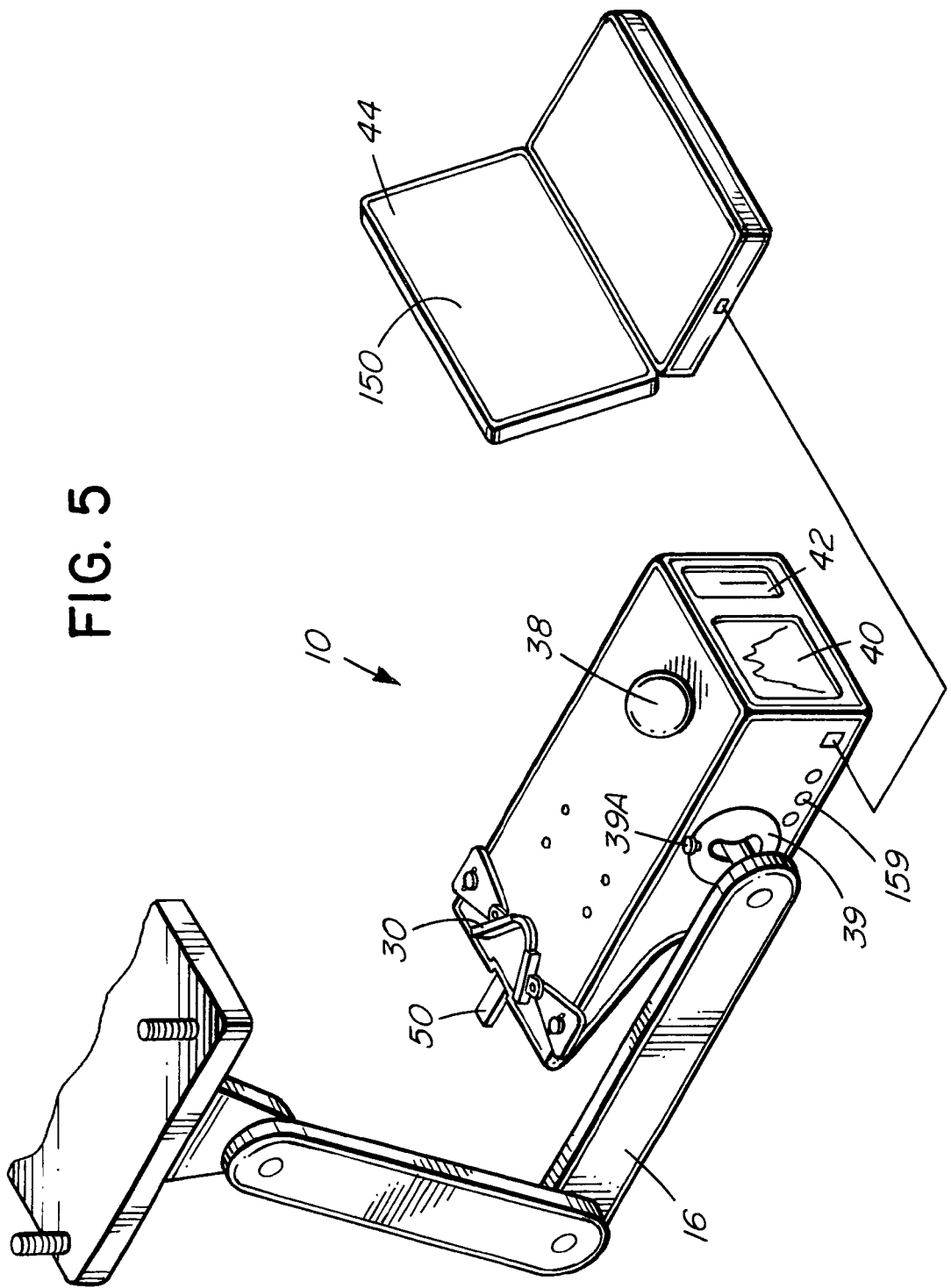

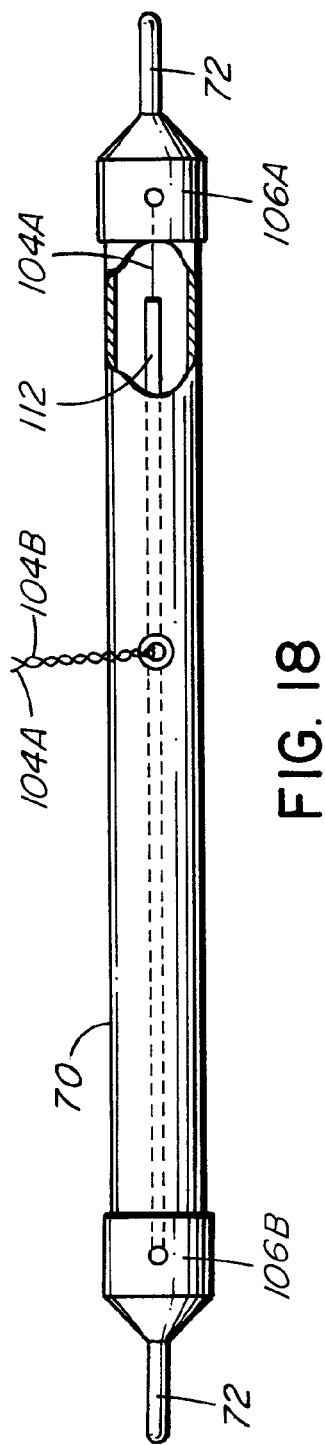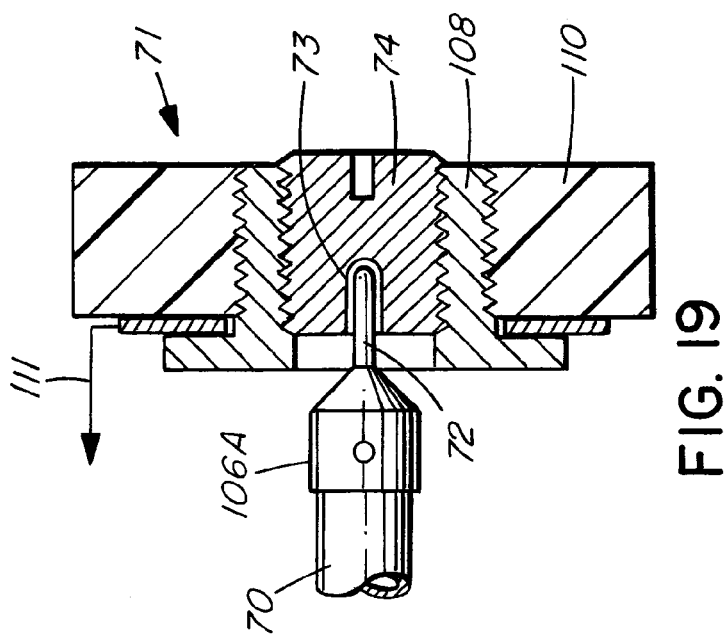

METHODS AND APPARATUS FOR MONITORING HEART MOTIONS

CROSS-REFERENCE TO RELATED APPLICATION

This application is a continuation-in-part of U.S. patent application Ser. No. 11/207,704 filed on 22 Aug. 2005 which issued as U.S. Pat. No. 7,503,898 on 17 Mar. 2009.

TECHNICAL FIELD

This invention relates to methods and apparatus for non-invasively monitoring heart motions. The methods and apparatus are useful for the non-invasive monitoring of cardiac functions, in particular, but not exclusively, of human hearts.

BACKGROUND

Heart disease is a major cause of mortality. There is a need for methods and apparatus that will permit the early detection of heart problems and for methods and apparatus capable of yielding information useful for diagnosing heart conditions.

Prior methods for the non-invasive monitoring of cardiac function have included:
- Mechanical methods, for example, pulse recording of the jugular carotid artery or apex cardiography.
- Electrical techniques, for example, electrocardiograms (ECGs).
- Imaging techniques, including echocardiology, radiography and magnetic resonance imaging (MRI).

Existing mechanical methods can be inaccurate because of physical differences between subjects. For example, the intensity of heart sounds is not a good measure of heart function because physiological differences between subjects, such as differences in thickness of layers of fat in the subjects, affects the intensity of heart sounds.

Electrical techniques suffer from the disadvantage that it is difficult to correlate the measured electrical signals with the force of cardiac contraction. Imaging techniques are also subject to this problem. For example, an echocardiogram determines a ratio known as the "ejection fraction". In a normally-functioning heart the ejection fraction may be related to the force of the heart's contraction. However, if the heart is not functioning normally then this relationship may fail to hold true.

None of the above-mentioned prior methods or techniques can accurately characterize the isovolumic phase of the heart cycle. Characteristics of the isovolumic phase can be important in identifying coronary artery disease and other heart-related conditions.

Pinchak, ESOPHAGEAL ACCELERATION AND THE CARDIOVASCULAR SYSTEM, Journal of Sound and Vibration, 1979, pp. 369-373 evaluates the use of miniature accelerometers within a stethoscope.

Koblanski, U.S. Pat. No. 5,865,759, the disclosure of which is incorporated herein by reference, discloses an apparatus and method for assessing cardiac function in human beings. The apparatus provides a sensing mechanism positioned on the thyroid cartilage in the neck against the trachea for sensing a response of the thyroid cartilage to heart function. A restraining system is provided to hold the sensing mechanism in position. It has been found that the apparatus, while useful, has several disadvantages including:
- the apparatus is undesirably sensitive to the posture of the subject;
- the apparatus can fail to detect accurately low-magnitude heart motions that occur immediately after a larger-amplitude heart motion;
- the signal-to-noise ratio is undesirably low;
- properly adjusting the restraining system is undesirably difficult; and,
- the system can provide erroneous results if parts of the system contact obstacles such as clothing, pillows, beards, fatty neck tissue, or the chest.

There remains a need for practical methods and apparatus for monitoring heart motions.

SUMMARY

The following embodiments and aspects thereof are described and illustrated in conjunction with systems and methods which are meant to be exemplary and illustrative, not limiting in scope.

One aspect of the invention provides a method for non-invasively monitoring motions of a subject's heart. The method comprising: applying a bias force to bias a probe against an anatomical structure of the subject in a first direction; allowing the probe to move against the bias force in response to motions of the subject's heart; and, measuring motions of the probe.

Another aspect of the invention provides apparatus for non-invasively monitoring motions of a subject's heart. The apparatus comprises a probe adapted to bear against an anatomical structure of the subject. The probe is moveable in a first direction in response to heart motions of the subject. The apparatus also comprises a movement sensor, which may comprise an accelerometer, connected to sense motions of the probe in the first direction. A bias mechanism is coupled to bias the probe in the first direction against the anatomical structure.

A mechanical motion amplifier may be provided between the probe and the motion sensor. The mechanical motion amplifier may comprise a lever having a pivot axis between the probe and the motion sensor. The pivot axis or motion sensor may be movable along the lever to adjust a gain of the mechanical motion amplifier.

The apparatus may comprise displays showing waveforms of both acceleration and displacement of the probe. In such embodiments, the acceleration and the displacement of the heart motions are simultaneously displayed in real time and can be observed to detect any irregularities of the heart motion.

Further aspects of the invention and features of various example embodiments of the invention are described below and shown in the accompanying drawings.

BRIEF DESCRIPTION OF THE DRAWINGS

In drawings which illustrate non-limiting embodiments of the invention:

FIG. 1A is a schematic view illustrating the interaction of the probe of the heart monitoring apparatus of FIG. 1 with the aortic arch of the subject;

FIG. 5 is a perspective view of the apparatus of FIGS. 1-4;

FIG. 18 is a side view of a pivotable support member;

FIG. 19 is a cross section view of a pivot supporting one end of the support member of FIG. 18;

DESCRIPTION

Throughout the following description specific details are set forth in order to provide a more thorough understanding to persons skilled in the art. However, well known elements may not have been shown or described in detail to avoid unnecessarily obscuring the disclosure. Accordingly, the description and drawings are to be regarded in an illustrative, rather than a restrictive, sense.

Measurement of the heart's motion, such as its acceleration, provides valuable insights into the condition of the heart. The motion of the heart is caused by forces which arise from changes in momentum of the heart mass and the ejection of blood during the various phases of the heart cycle. Heart abnormalities can cause the pattern and the amplitude of these forces to change, thereby yielding diagnostic value.

The heart generates both strong and weak forces, which can all have diagnostic significance. The methods and apparatus described herein enable the measurement of both systolic and diastolic phases of the heart cycle. The apparatus can be applied to obtain measurements that characterize the isovolumic phase (i.e. the heart's contraction before the valves of the heart are open) of a subject's heart cycle. Isovolumic contraction is strongly correlated to the ejection phase in magnitude and duration. As an example of a valuable diagnostic result that can be obtained by monitoring heart motion, a large force of contraction in the isovolumic phase combined with a low-magnitude ejection is a strong indicator that stenosis of the aortic valve exists.

This invention provides non-invasive methods for monitoring motions of a subject's heart. The methods comprise placing a probe against an anatomical structure (for example, the tracheal cartilage or the aortic arch) that moves in response to heart motions. The probe is biased into contact with the anatomical structure by a bias force which acts in a direction that is generally parallel to heart-induced motions of the anatomical structure. In some embodiments, the probe is connected to a motion sensor (such as an accelerometer) by a mechanical amplifier that amplifies the motion of the probe and applies the amplified motion to the motion sensor.

Figure 1:
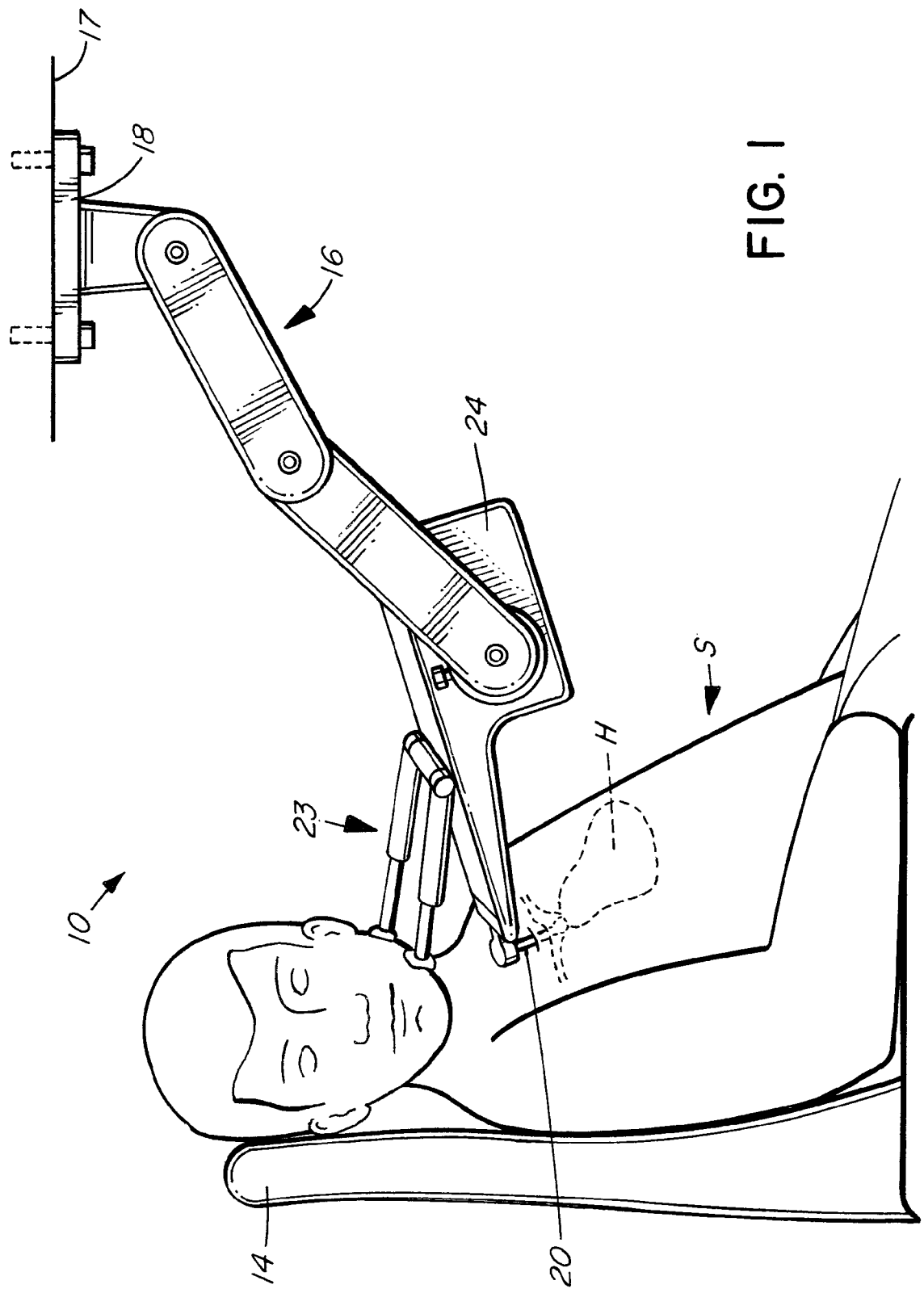
FIG. 1 is a side elevation view of a heart monitoring apparatus coupled to monitor motion of the aortic arch of a seated subject.

FIG. 1 shows heart monitoring apparatus 10 according to an embodiment of the invention. Apparatus 10 is configured to measure heart forces at the brachiocephalic region of the aortic arch. As described below, apparatus 10 may be configured, in the alternative, to measure heart forces at alternative anatomical structures, such as at the thyroid cartilage region of the trachea.

The aortic arch is a good point at which to measure heart forces since measurements at this location can provide much information on all of the phases of the heart cycle including atrial contraction. Measuring heart forces at the aortic arch is also convenient in the operating room as good measurements can be obtained while the subject is lying in a natural posture. Heart motion can be measured by monitoring motion of the brachiocephalic area of the aortic arch in most mammals.

Apparatus 10 is shown in coupled relationship with the aortic arch of the chest of a subject S seated in a chair 14. Apparatus 10 is carried by a support device 16 mounted to a ceiling 17 by a support plate 18. Support device 16 permits apparatus 10 to be readily manoeuvred and adjusted in position relative to subject S. Support device 16 may comprise an overhead carriage and swivel mechanism of a type similar to that employed to support overhead lamps of the types used in operating theaters or in dentists' offices. A wide range of suitable support mechanisms are well known and are therefore not described in greater detail herein.

Figure 2:
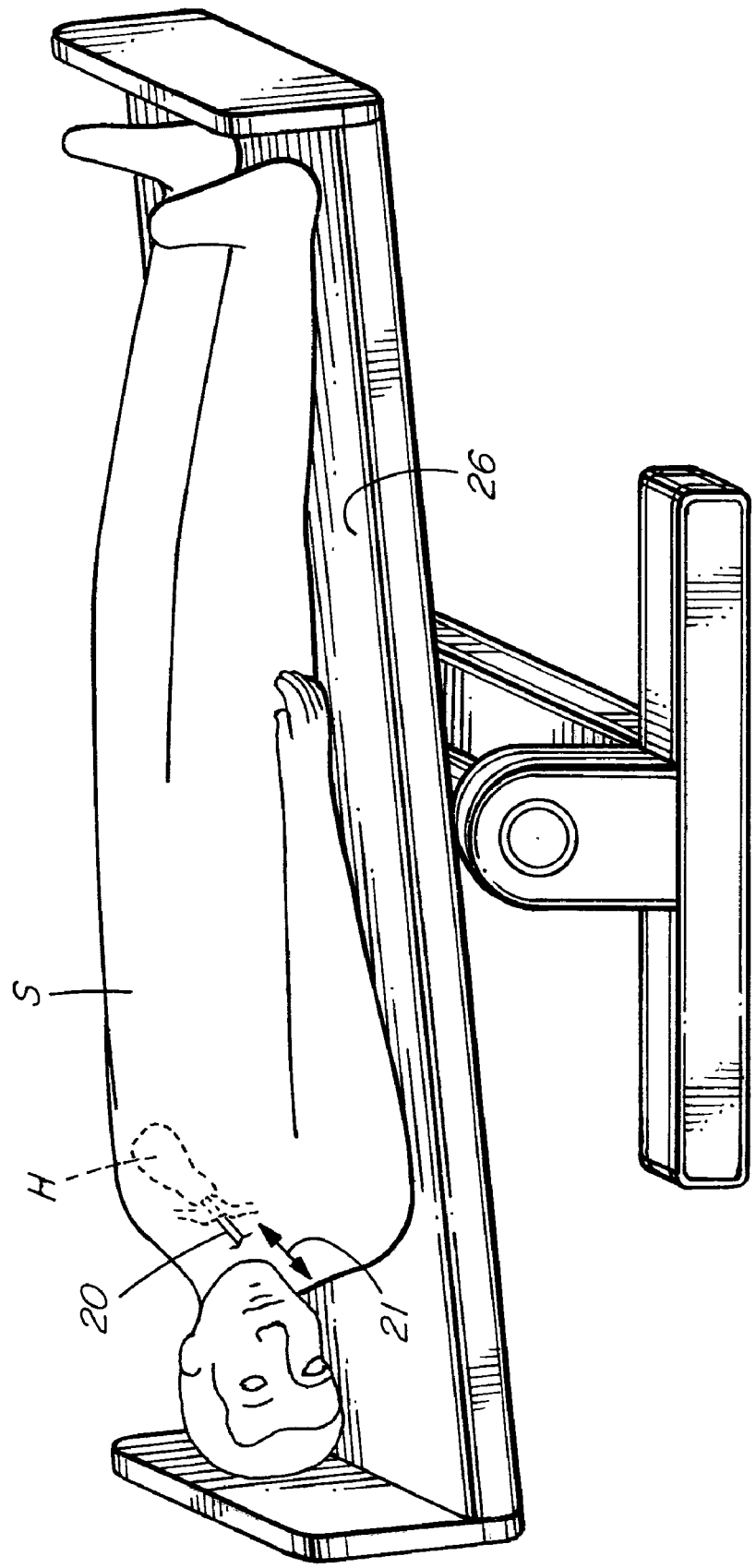
FIG. 2 is a view showing the probe of the apparatus of FIG. 1 coupled to monitor motion of the aortic arch of a subject in a prone posture.

Apparatus 10 is moved into a position which makes it possible to couple a probe 20 (see FIG. 1 A) to sense heart forces applied to an anatomical structure of a subject. The anatomical structure may comprise, for example, the aortic arch or the thyroid cartilage of subject 12. FIGS. 1, 1A and 2 show apparatus 10 configured to detect motions of the aortic arch A of subject 12. Aortic arch A is moved in response to motions of the subject's heart H. FIG. 1A shows that probe 20 can be guided behind the right-hand side of the subject's manubrium M, substantially parallel to the main axis of the heart, between the jugular and the clavicular notch at an angle of roughly 45° to the subject's neck. Support device 16 is external to subject S and holds probe 20 in position relative to a base (e.g. plate 18) on which apparatus 10 is mounted.

To facilitate introduction of probe 20, the subject's head is rotated to the right. The subject is asked to inhale deeply several times as probe 20 is advanced to a depth at which probe 20 is adjacent to aortic arch A and a record is obtained. This typically involves insertion of probe 20 to a depth of more than about 1½ inches (about 3¾ cm) below a top edge of manubrium M. In typical adult subjects, probe 20 can be coupled to move with the brachiocephalic region of the arch of the aorta when probe 20 is at a point approximately 2 inches (about 5 cm) below the top edge of manubrium M. As probe 20 approaches aortic arch A it will begin to move in direction 21 in a pattern that is periodic with the subject's heartbeat. The position of probe 20 may be adjusted while monitoring the amplitudes of detected heart motions until the heart motion amplitude is maximized.

Probe 20 is biased toward heart H by a bias mechanism. Various bias mechanisms are described below. The bias mechanism keeps probe 20 coupled to move with aortic arch A by applying a continuous force directed along probe 20 in direction 21. Probe 20 moves in direction 21 in response to motions of aortic arch A.

A jaw and head support 23 is provided on a housing 24 of apparatus 10. Jaw and head support 23 is adjusted to contact the subject's jaw and the base of the subject's skull when probe 20 is coupled to the brachiocephalic region of the subject's aortic arch. The subject can rest his or her head against jaw and head support 23 while apparatus 10 monitors motions of probe 20.

FIG. 2 shows apparatus 10 in use on a subject S, with his head turned to the right, on a tiltable platform 26. Probe 20 is coupled to the aortic arch of subject S. Jaw and head support 23 (not shown in FIG. 2) is employed to prevent apparatus 10 from moving relative to subject S. Platform 26 can be tilted so that the subject's head is inclined slightly downwardly. This assists in maintaining good coupling between probe 20 and the subject's aortic arch and also prevents blood from pooling in the subject's legs in a manner that could affect the subject's circulation. The posture shown in FIG. 2 causes the abdominal organs to push against the subject's diaphragm. This, in turn, pushes the chest organs so that the aortic arch moves closer to the top edge of the manubrium so that it can be more easily accessed by probe 20. Having the subject in the supine posture as shown in FIG. 2 is a good arrangement for various operating theatre settings, as the subject can be on his or her back. The subject's head should be turned to the right, as shown.

Lung resistance can influence the motion of the heart. Lung resistance should therefore be measured in conjunction with using apparatus 10 to determine the performance of the heart. The lung resistance can be taken into consideration when interpreting measurements obtained by apparatus 10. Lung resistance can be tested by asking a subject to breathe fairly rapidly while monitoring the displacements detected by apparatus 10. The higher the amplitude of the displacement corresponding to the subject's breaths, the higher the resistance of the lung is gauged to be. The displacement may be detected electronically and recorded or observed on a display provided on apparatus 10.

Figure 3:
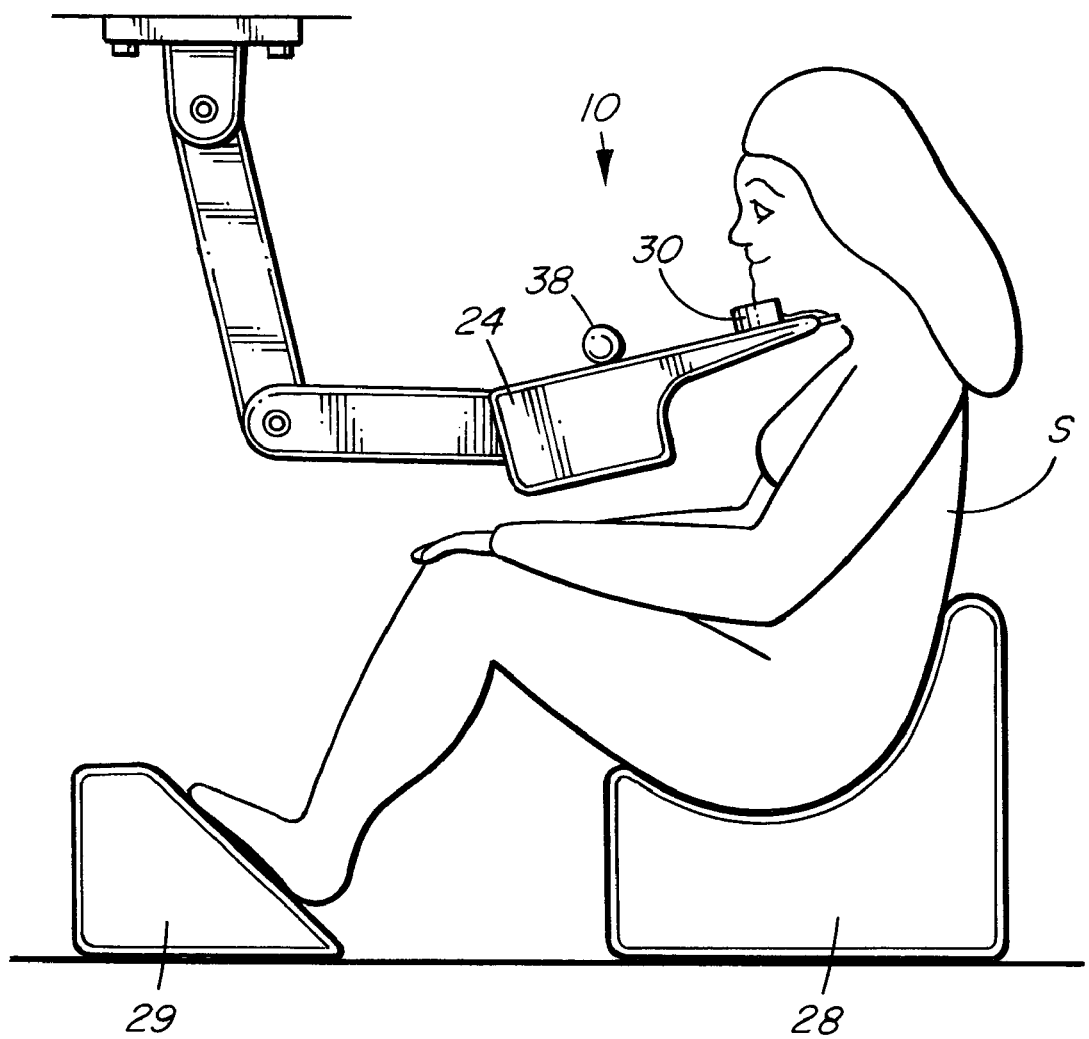
FIG. 3 is a side elevation view of the apparatus of FIG. 1 coupled to measure motions of the thyroid cartilage of a seated subject.
Figure 4:
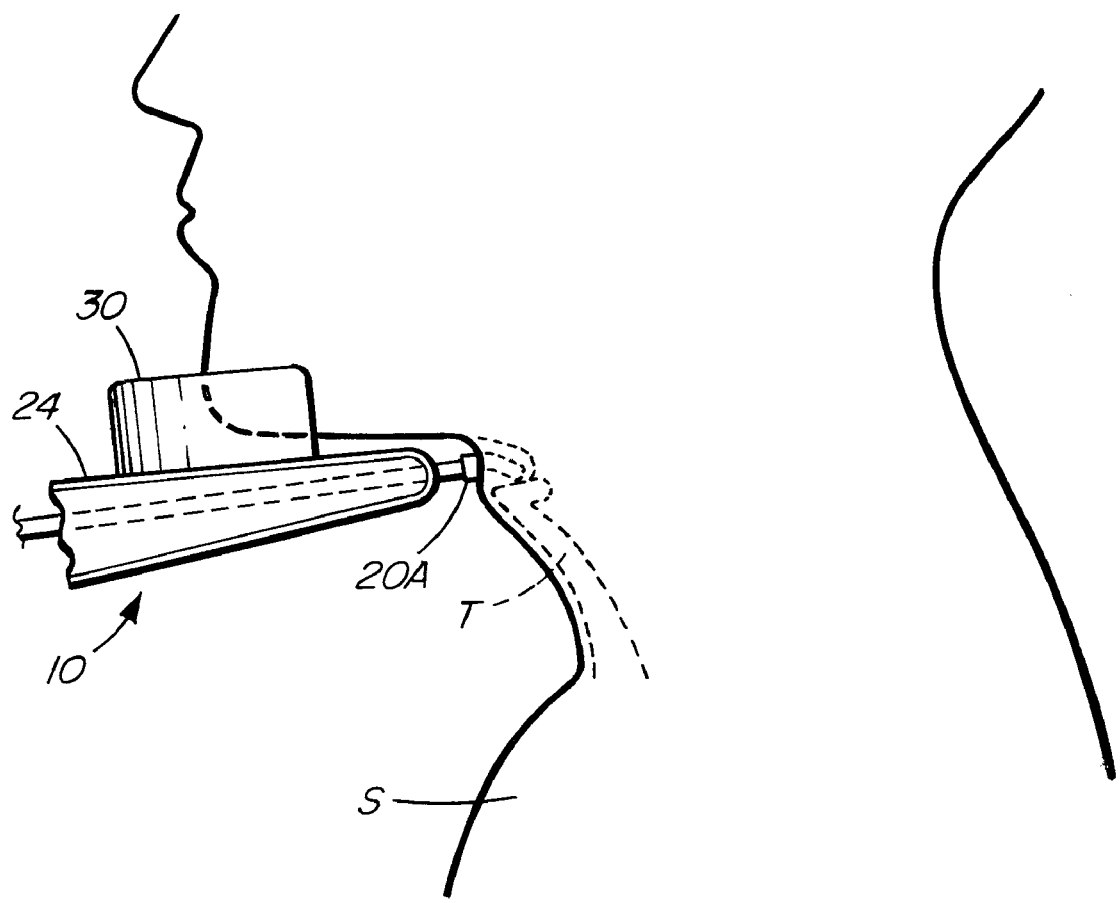
FIG. 4 is a schematic view illustrating the interaction of the probe of the heart monitoring apparatus of FIG. 3 with the thyroid cartilage of the subject.

FIGS. 3 and 4 show apparatus 10 configured to monitor heart-induced motion of the thyroid cartilage of a subject S. Subject S is seated on a seat 28 with her feet on an elevated foot rest 29. In this posture the abdomen is somewhat pressurized. Thyroid cartilage motion may also be measures while the subject is in other postures, for example, a subject may be in a head-down posture on a tiltable table as shown in FIG. 2 while motion of the thyroid cartilage is monitored. The top of housing 24 is adjusted to be parallel to the subject's jaw. Probe 20 (see FIG. 1) has been replaced with a probe 20A. Probe 20A engages the top edge of the subject's thyroid cartilage T at the subject's thyroid notch N. Probe 20A is biased downwardly against the top of the subject's thyroid cartilage by a spring or other bias mechanism as described below.

While apparatus 10 monitors motion of the subject's thyroid cartilage, the subject's chin rests on a U-shaped chin rest 30 on housing 24. Chin rest 30 may be removable so that it does not interfere with the use of jaw and head support 23 when apparatus 10 is being used to monitor motion of a subject's aortic arch. In the illustrated embodiment, plates 31 are pivotally connected to opposite sides of chin rest 30. Adjustment screws 32 are inserted through slots 33 in plates 31 into threaded engagement with housing 24. Chin rest 30 can be adjusted to contact the subject's chin. Screws 32 can then be tightened to prevent chin rest 30 from moving. Screws 32 may be removed to permit removal of chin rest 30.

In FIG. 3, the subject's head is bent towards the chest and the feet raised close to the body to raise the pressure in the subject's abdomen. Motion of the subject's thyroid cartilage could also be measured with subject 12 lying head-down on an inclined table, as shown in FIG. 2.

Figure 4A:
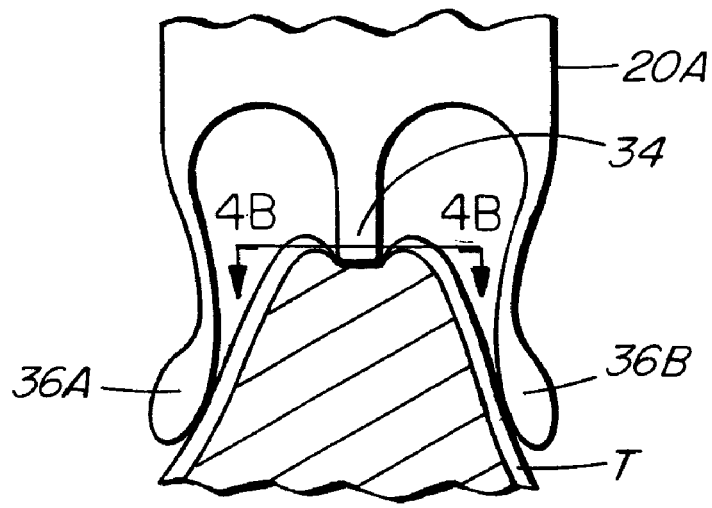
FIGS. 4A, 4B and 4C are respectively top plan, partial cross sectional and side views of a probe that may be used for coupling a heart monitoring apparatus to measure motions of the thyroid cartilage of a subject.
Figure 4B:
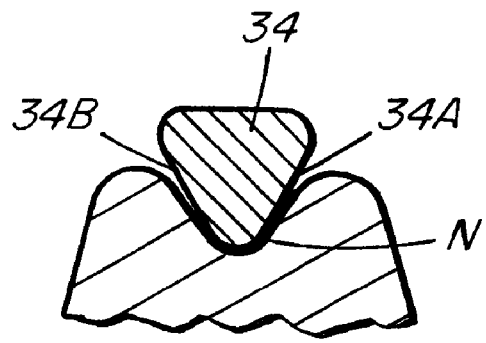
Figure 4C:
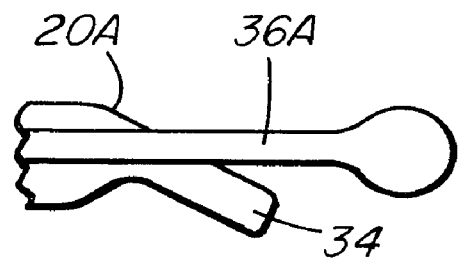

As shown in FIGS. 4A, 4B and 4C, probe 20A has a projection 34 that can engage the upper edge of the subject's thyroid cartilage. Projection 34 preferably has inclined or rounded side faces 34A and 34B that help to keep projection 44A centered on the subject's thyroid notch N. Projection 34 is inclined at a slight downward angle in the illustrated embodiment. Probe 20A may comprise arms 36A and 36B that engage the subject's neck adjacent to the sides of the subject's thyroid cartilage. Arms 36A and 36B help to keep probe 20A centered from side-to-side on the subject's thyroid cartilage. Arms 36A and 36B may be resilient. Arms 36A and 36B and projection 34 may be coated with an elastomeric material for comfort of the subject and for preventing irritation of the subject's skin. Probe 20A may have other configurations that permit it to engage the upper edge of a subject's thyroid cartilage.

While apparatus 10 has been described as being configurable for measuring heart motion at either the aortic arch or the thyroid cartilage, an apparatus according to the invention could be constructed specifically for measuring heart motion at only one of these sites or at some other suitable anatomical site.

FIG. 5 shows details of a heart motion measurement apparatus 10 according to a specific example embodiment of the invention. A handle 38 is provided on housing 24. Apparatus 10 can be guided into a desired position by manipulating handle 38. Housing 24 is connected to support device 16 by a ball joint 39 so that housing 24 can be tilted as desired. Ball joint 39 has a lock screw 39A for fixing housing 24 in a desired position relative to support device 16.

A display 40 is provided on housing 24 or at another convenient location. Display 40 can display information about the status of apparatus 10 as well as information about the motion of the subject's heart as measured by apparatus 10. For example, display 40 may display a waveform showing the displacement of a subject's heart as a function of time, and may include a displacement magnitude display 42 for displaying the magnitude, or amplitude, of the displacement whose waveform is shown by display 40.

Apparatus 10 may be connected to a computer 44. Computer 44 may comprise a laptop computer, a personal computer, or a computer network. Computer 44 may receive data from apparatus 10. The data may comprise data representing heart motion and may also include other data. The data may be stored, manipulated, displayed or otherwise processed by computer 44.

In the illustrated embodiments, probe 20 (or 20A) is mounted on an end of a lever 50 that projects from housing 24. Apparatus 10 includes a bias means, such as a spring, as described in more detail below. The bias means biases the probe toward the subject's aortic arch or other part of the subject's anatomy and thereby maintains good coupling between probe 20 and the subject's anatomy. Correct coupling of probe 20 with the subject's aortic arch in the brachiocephalic region will be indicated by a strong pivotal movement of lever 50.

Apparatus 10 includes a sensor that detects motion of lever 50. Motions of the subject's heart are transferred to the subject's aortic arch (which is directly connected to the heart). Motions of the aortic arch are transferred to lever 50 by probe 20. Measured motions of lever 50 are therefore directly correlated to motions of the subject's heart. Apparatus 10 can record, process and/or display these motions and/or values derived from these motions as described in more detail below.

Figure 6:
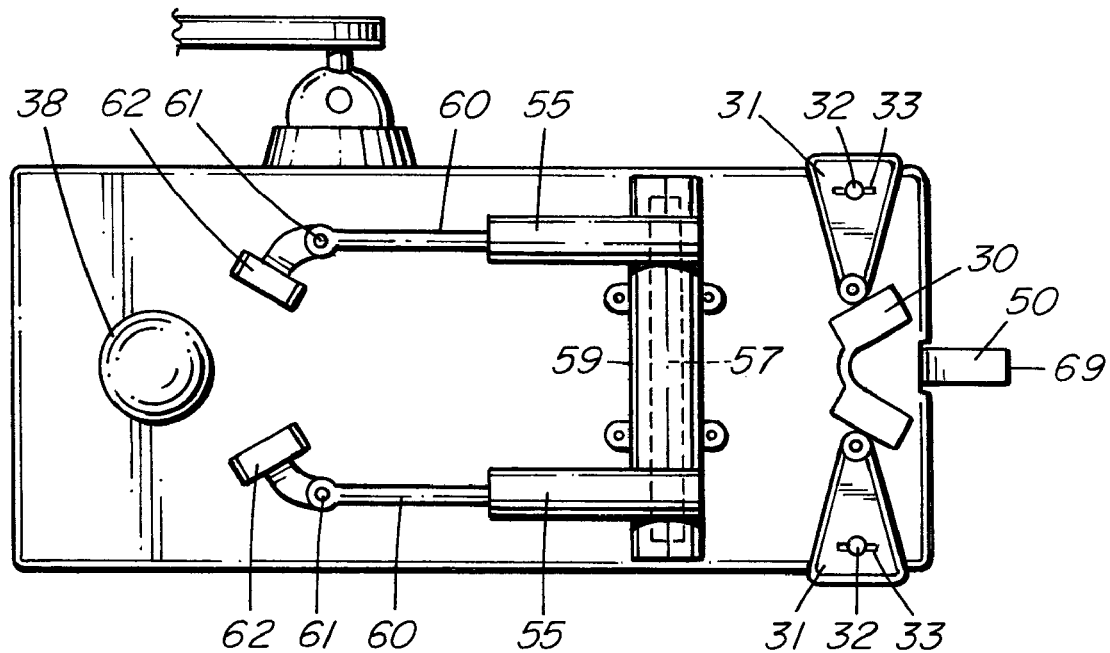
FIGS. 6 and 7 show plan views of parts of the apparatus of FIGS. 1-4, with a chin rest and a jaw and head rest.
Figure 7:
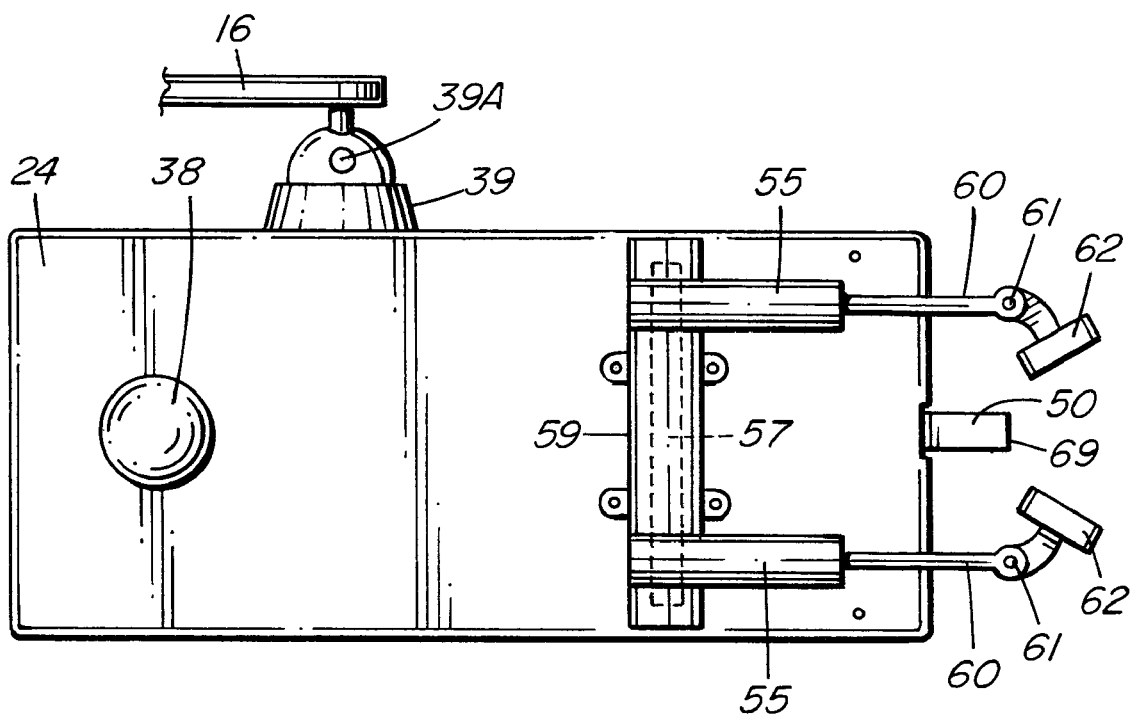
Figure 10:
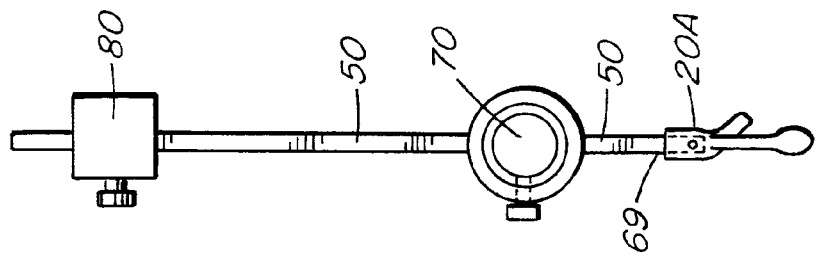
FIG. 10 is a view corresponding to that of FIG. 9, but with the probe replaced by a different probe for coupling to the thyroid cartilage.
Figure 9:
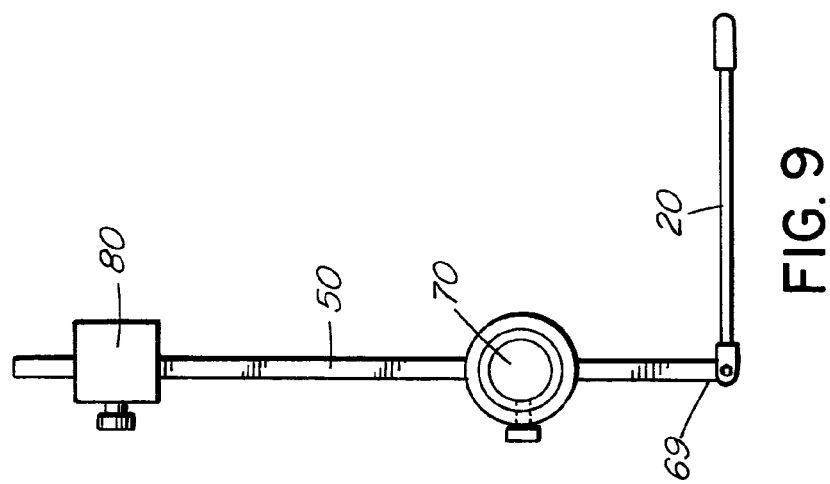
FIG. 9 is a side view of the components of the apparatus shown in FIG. 8, with a probe connected to the effort section of the lever for coupling to the aortic arch.

As shown in FIGS. 6 and 7, jaw and head support 23 includes a pair of arms 55 which are each pivotally secured at one end to a shaft 57. Shaft 57 is pivotally secured to housing 24. In the illustrated embodiment, shaft 57 passes through a sleeve 59. At its opposite, free end 60, each of the arms 55 is connected by a pivot 61 to a pad 62. Pads 62 rest on the subject when jaw and head support 23 is in use.

By pivoting shaft 57 and arms 55 relative to the housing 24, jaw and head support 23 can be moved between an inoperative position, in which it is shown in FIG. 6 and in which the arms 55 lie above the housing 24, and an operative position, in which it is shown in FIG. 7, and in which the arms 55 and their pads 67 project beyond the end of housing 32 at which lever 50 protrudes. Jaw and head support 23 is shown in its operative position in FIG. 1.

When it is desired to measure motion of the subject's thyroid cartilage, jaw and head support 23 may be moved to its inoperative position and chin support 30 may be mounted on housing 24 and adjusted to fit the subject after handle 38 has been manipulated to move probe 20A into contact with the top edge of the subject's thyroid cartilage. Correct coupling of probe 20A with the subject's thyroid cartilage will generally be indicated by visible rhythmic pivoting of lever 50. By removing chin rest 30 and pivoting jaw and head support 23 into its operative position shown in FIG. 7, and by replacing probe 20A with probe 20, apparatus 10 can be prepared for coupling to the aortic arch of a subject.

In the illustrated embodiment, probe 20 or 20A mounts to a distal end 69 of lever 50. Lever 50 is supported on a support member 70 that is pivotally mounted in housing 24. From FIG. 18, it can be seen that each end of support member 70 is journalled in a pivotal support 71 formed between a pin 72 on an end of support member 70 and a socket 73 in a screw 74 supported in housing 24. A probe (e.g. 20 or 20A) is displaced by movements of the relevant part of the subject's anatomy resulting from the subject's heart motion. These movements cause lever 50 and support member 70 to pivot about the longitudinal axis of the support member 70.

Figure 8:
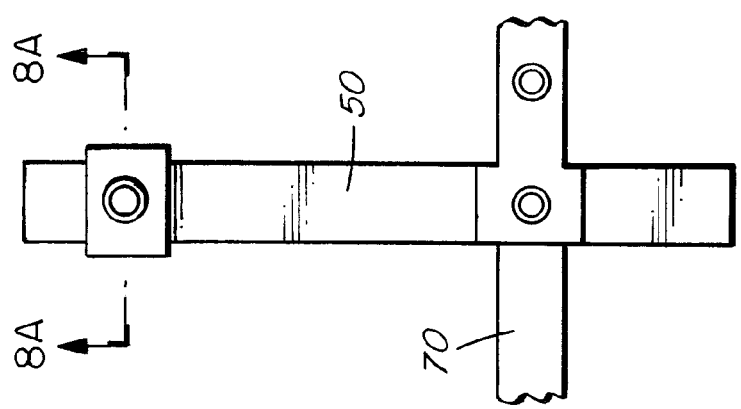
FIG. 8 is a broken-away view of a lever and a pivotable support member pivotally supporting the lever.
Figure 8A:
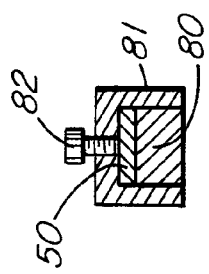
FIG. 8A is a view taken in section along the line 8A-8A of FIG. 8.

An accelerometer 80 (FIG. 8a) is fixed to a U-shaped bracket 81. A locking screw 82 is provided for releasably securing bracket 81 and, therewith, the accelerometer 80 at a desired position along lever 50. The position of accelerometer 80 along lever 50 can be adjusted by loosening screw 82 and sliding bracket 81 to a desired position along lever 50. It can be appreciated that lever 50 provides mechanical amplification of any motion of the distal end 69 of lever 50 to which probe 20 or 20A is coupled. The amount of amplification can be adjusted by sliding the accelerometer to a desired position along lever 50. This adjustment may be used to compensate for the fact that different accelerometers tend to produce different electrical outputs for the same acceleration. Accelerometer 80 may be mounted at such a position along lever 50 that it produces a desired output when the distal end 69 of lever 50 is moved with a specified acceleration.

Apparatus 10 may be calibrated by coupling lever 50 to a vibrator that provides a predetermined acceleration. The position of accelerometer 80 along lever 50 can be adjusted until the output of the output signal of accelerometer 50 has a desired value.

In the illustrated embodiment, lever 50 serves as a mechanical motion amplifier. Support member 70 serves as a fulcrum. Lever 50 and support member 70 are pivotable about a pivot axis in response to movements of probe 20 or 20A, which is provided at one end of an effort section of lever 50. Accelerometer 80 is provided at an end of a load section of lever 50 on a side of the pivot axis opposed to the effort section. The pivot axis is located between probe 20 and accelerometer 80.

If the load and effort sections of lever 50 are unequal in length then the point on lever 50 at which accelerometer 80 is located will move more or less than the point at which probe 20 acts on lever 50. When the load section is longer than the effort section, lever 50 amplifies the movements of probe 20, which correspond to the movements of the subject's anatomy. The electric signal output by accelerometer 64 may be amplified and condition as required.

Providing an adjustable mechanical amplification can be used to largely eliminate inter-instrument differences, and enable comparison of data results between similar apparatus 10 at different centres of clinical research. The mechanical amplification provided, for example, by lever 50, can contribute to improved signal-to-noise ratios in comparison to apparatus that provides only electrical amplification of the signal output by an accelerometer.

Figure 11:
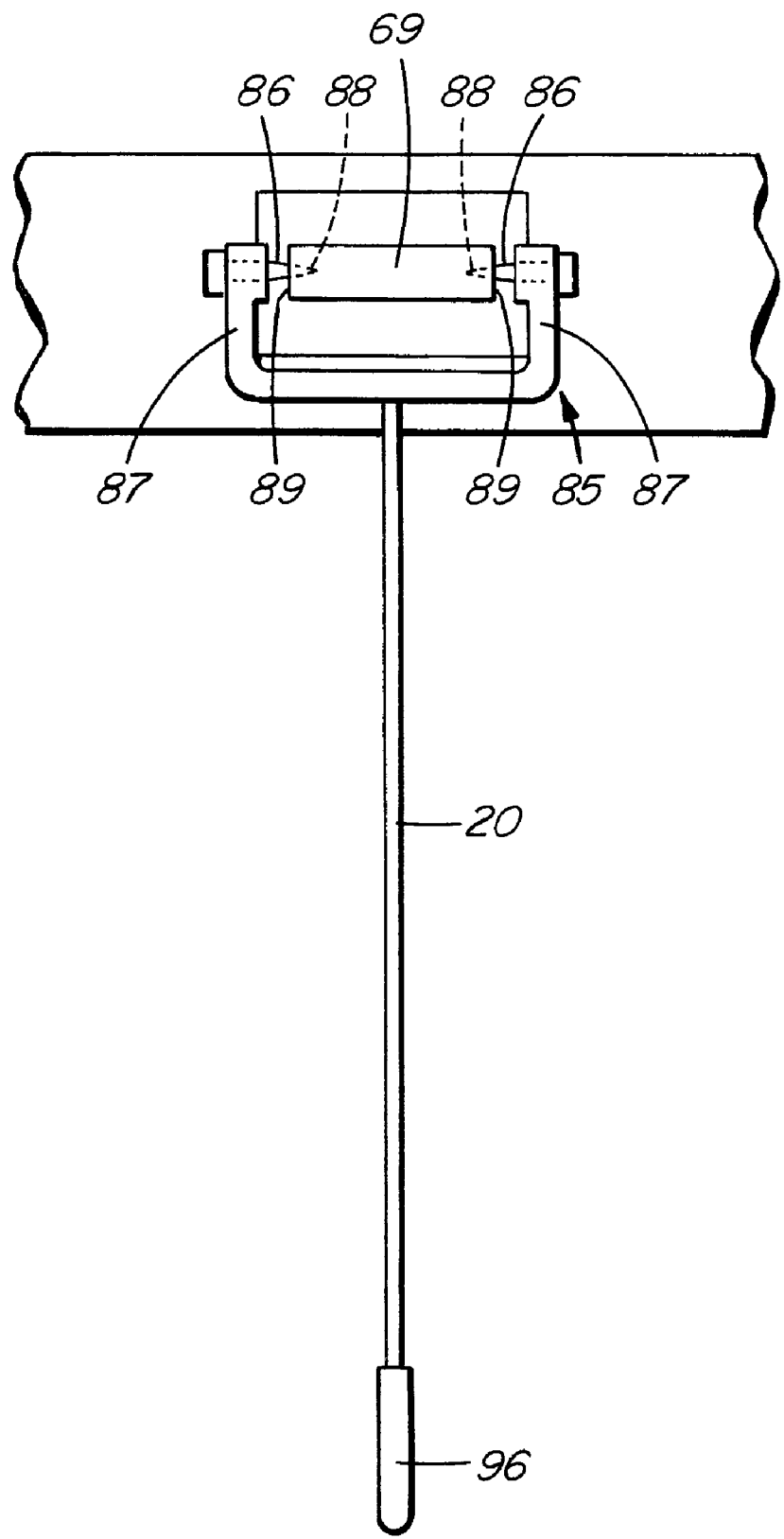
FIG. 11 is a front elevation view of the apparatus of FIG. 9.

As shown in FIG. 11, probe 20 may comprise a rod which at one end has a bifurcated end portion indicated generally by reference numeral 85. A pair of pivot pins 86 in threaded engagement with arms 87 of end portion 85 have pointed ends 88 pressed into opposite longitudinal edges 89 of end portion 69 of lever 50. Probe 20 is thereby pivotally coupled to lever 50. Longitudinal movement of probe 20 causes lever 50 to pivot.

Figure 12:
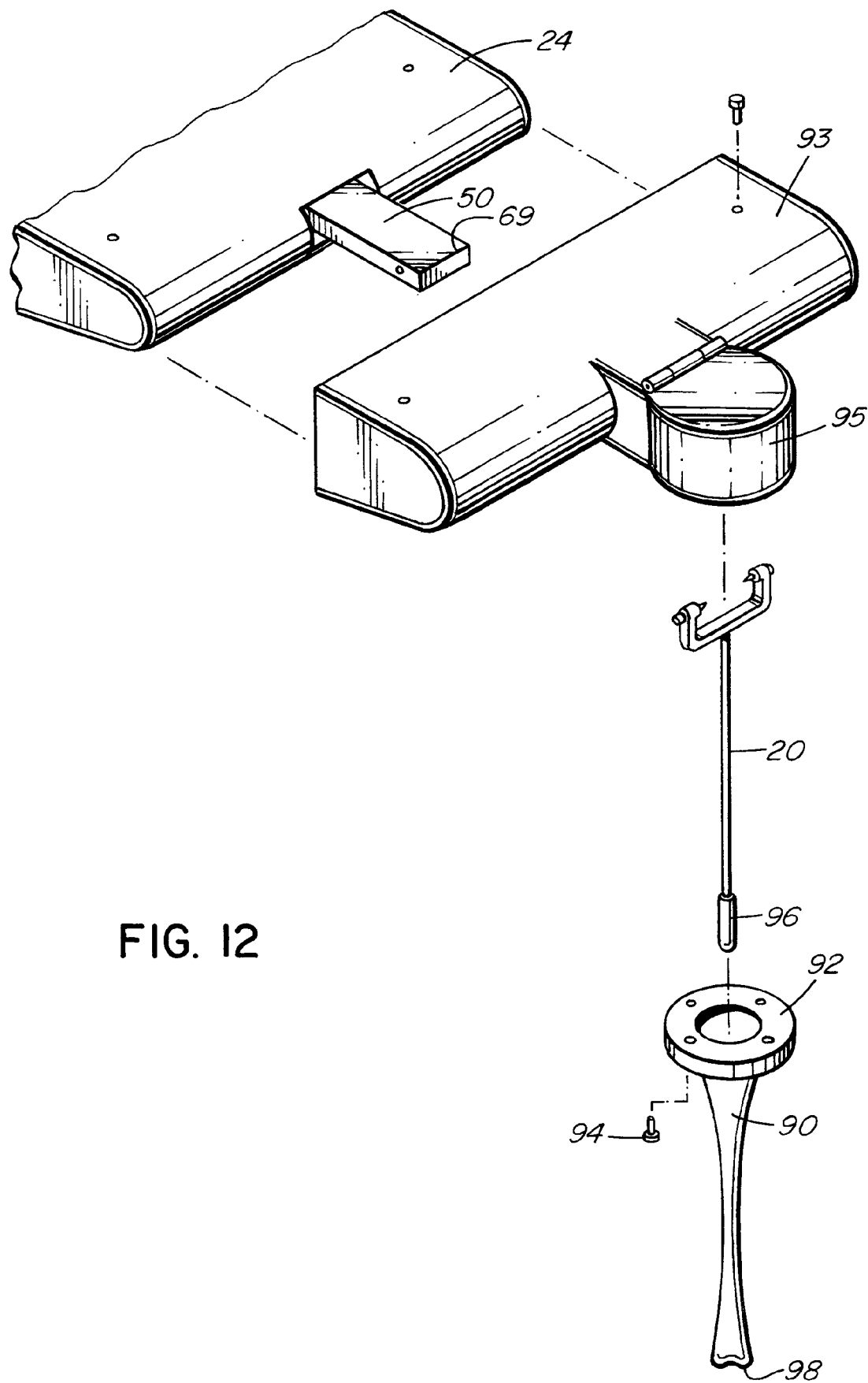
FIG. 12 is an exploded perspective view of apparatus that includes the parts shown in FIG. 11 with a protective sheath and a housing.

As shown in FIGS. 11 and 12, probe 20 extends through a protective housing 90. An annular end portion 92 of housing 90 is detachably mounted to a housing 93, for example, by means of screws 94 inserted through end portion 92 into threaded engagement with a protruding portion 95 of housing 93. Housing 93 is mounted to housing 24. The end portion 69 of lever 50 projects into protruding portion 95 of housing 93 where it couples to probe 20. A removable protective sheath 96 is fitted at the free end of probe 20, opposite from bifurcated end portion 85.

Figure 14:
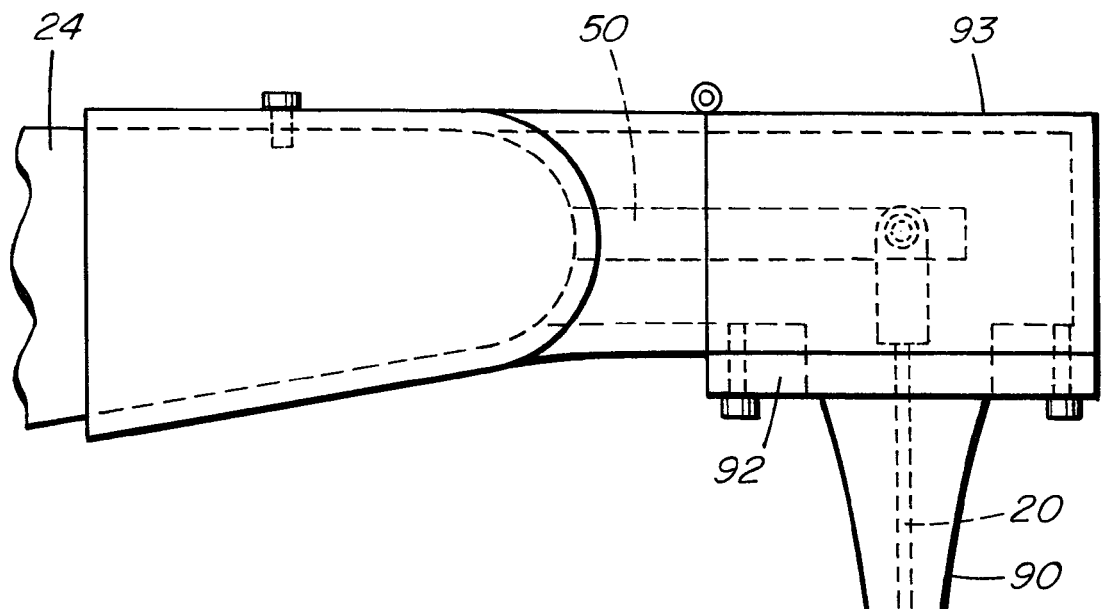
FIG. 14 shows a broken-away view of an end of the aortic arch probe of the apparatus of FIGS. 11 and 12 in coupling contact with the skin of a subject.
Figure 13:
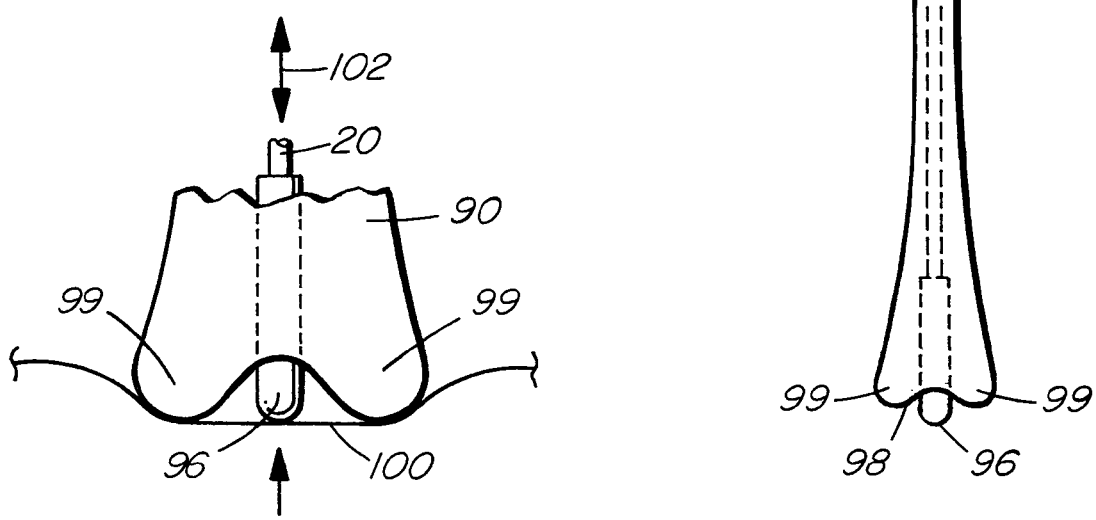
FIG. 13 is a side elevation view of the apparatus of FIG. 12.

As shown in FIG. 14, protective housing 90 has an open lower end portion 98, through which the tip of probe 20 (i.e. the tip of sheath 96) protrudes. Lobes 99 are provided on end portion 98 on either side of sheath 96. Lobes 99 may optionally be portions of a ring that extends around the end of probe 20 and is radially spaced-apart from probe 20. In use, the subject's skin 100 becomes stretched over lobes 99. Motion of the subject's aortic arch is transferred through the subject's skin 100 to the end of probe 20. In response, probe 20 reciprocates in the direction indicated by arrow 102.

Figure 21:
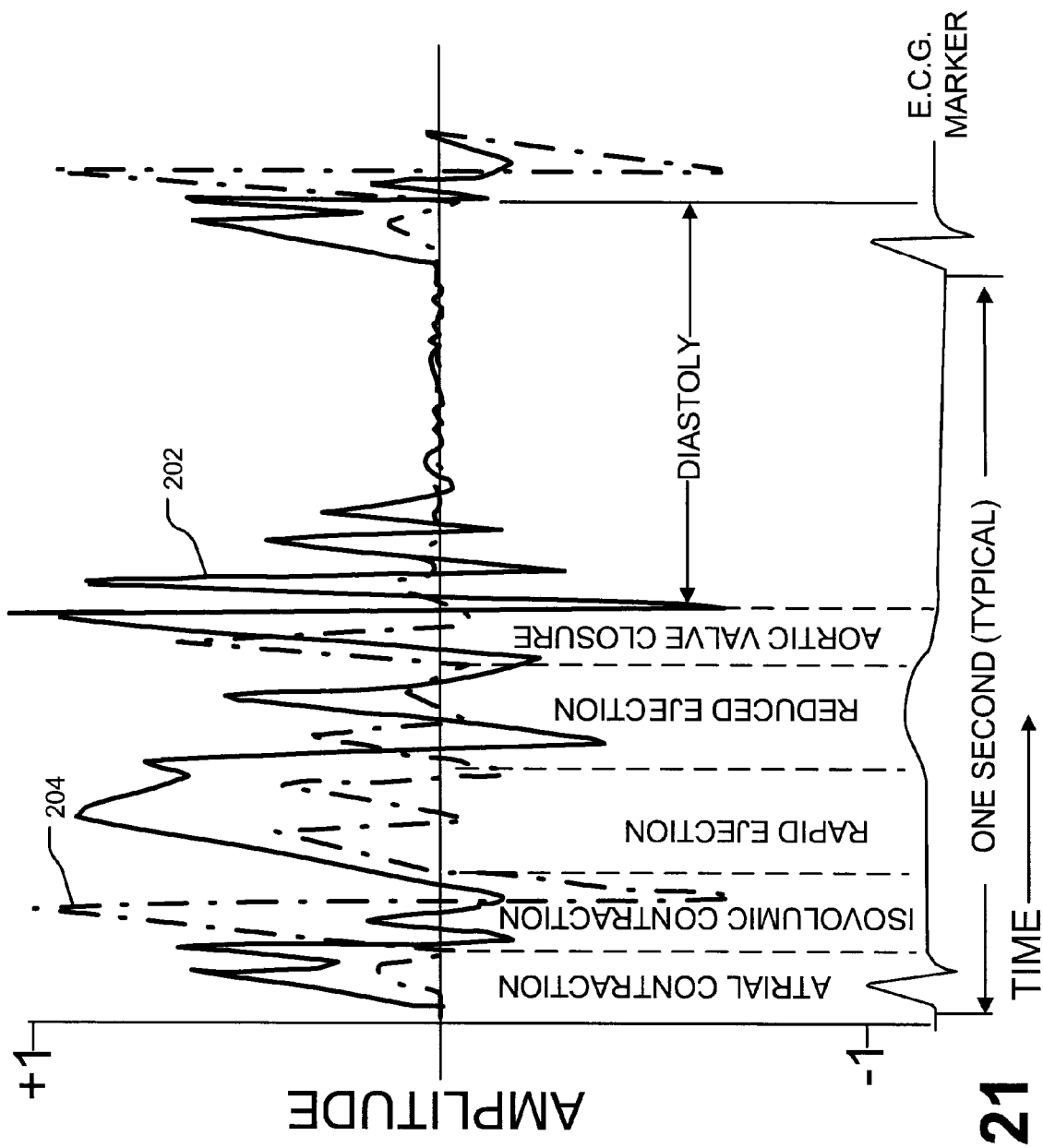

A pair of electrical conductors 104A and 104B carry electrical signals from accelerometer 80 to signal processing circuits. In the illustrated embodiment, the electrical signals are carried through the pivot mechanisms by which support member 70 is mounted in housing 24. FIG. 21 shows support member 70 in greater detail.

Support member 70 comprises a tubular member that is electrically non-conducting and is provided at opposite ends with end caps 106A and 106B from which protrude pivot pins 72. Each pivot pin 72 is pivotally received in a threaded grub screw 74 in threaded engagement with a threaded retainer 108 which, in turn, is in threaded engagement with a wall 110 of housing 24.

One conductor 104A from accelerometer 80 extends along the interior of tubular pivotal member 70 to a first one 106A of the end caps 106, which is electrically conductive. End cap 106A electrically connects conductor 104A through grub screw 72 to an electrical conductor 111, thereby providing an electrical connection without affecting the ability of pivotal member 70 to pivot freely. Electrical conductor 111 is connected to carry its signal to suitable signal processing circuits. Similarly, conductor 104B is connected to the signal processing circuits by way of the other electrically conductive end cap 106B. Within support member 70, conductors 104A and 104B extend along the interior of a tubular electrically-conducting shield 112 which is connected to end cap 106B.

Figure 15:
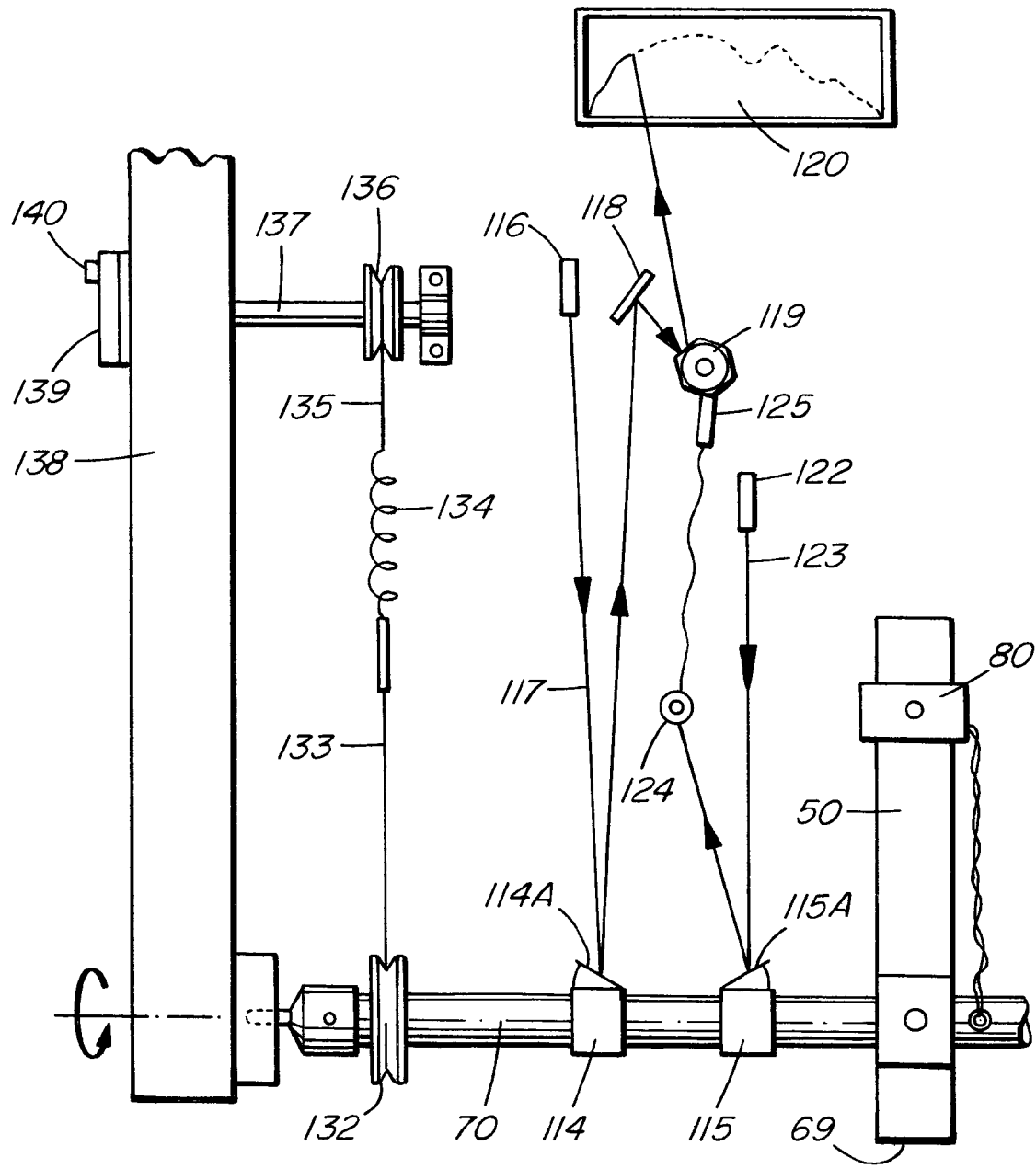
FIG. 15 is a diagrammatic view of parts of the apparatus of FIGS. 1-4, including mechanical and optical motion amplifying devices.

Apparatus 10 comprises optical motion amplifiers that provide alternative mechanisms for representing heart motions. These are illustrated in FIG. 15. In the illustrated embodiment, support member 70 carries a mounting 114 carrying a mirror 114A. A light source 116, which may comprise a laser, directs a light beam 117 onto mirror 114A. The reflected light beam is reflected by a mirror 118 and a rotating mirror 119 to a display screen 120 forming part of the display 40. Screen 120 is a phosphorescent screen of high persistence. The trace of light beam 117 on screen 120 represents the waveform of the displacement of the heart function being monitored.

A second mirror 115A is mounted to support member 70 by a mounting 115. A second light source 122, which may comprise a laser, directs a light beam 123 onto mirror 115A, from which light beam 123 is reflected onto a photosensor 124, such as a photodiode or phototransistor. A motor 125 that turns mirror 119 is controlled in response to an electrical signal from photosensor 124 by a suitable controller 121 (see FIG. 20) so that the rotation of mirror 119 is synchronized with the alternating pivoting movement of support member 70.

Figure 16:
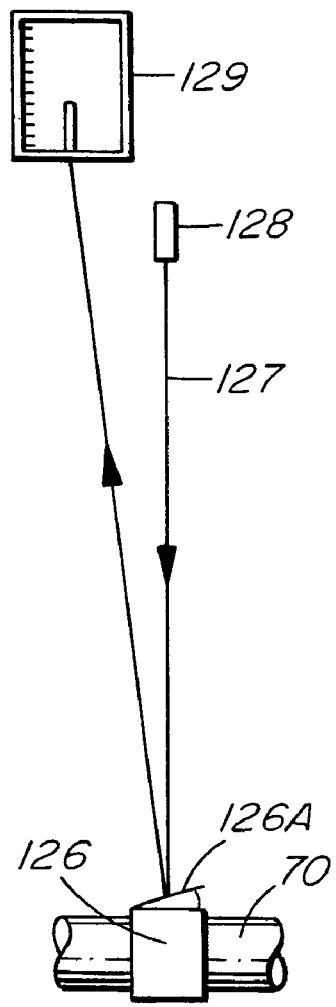
FIG. 16 and 17 diagrammatically illustrate two versions of an optical motion amplifying device.

Support member 70 may also carry a mounting 126 (FIG. 16) carrying a mirror 126A for reflecting a light beam 127 from a light source 128, such as a laser, onto a screen 129, which forms part of the display 40. Screen 129 is a phosphorescent screen of long duration. The magnitude of the displacement of the heart function can be observed by watching screen 129.

Figure 17:
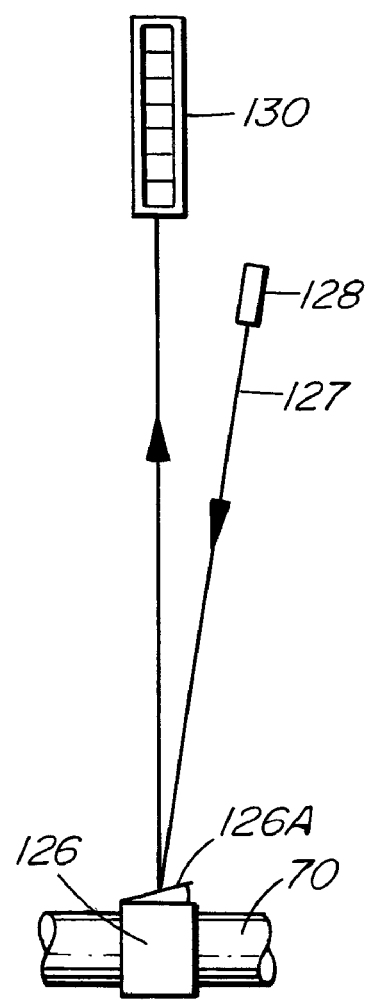

As shown in FIG. 17, screen 129 may be replaced by a position sensing diode array 130, which provides a digital output that indicates the deflection of beam 127 by mirror 126A.

As mentioned above, a bias mechanism causes support member 70 to pivot in a direction such that probe 20 or 20A is biased against a portion of the subject's anatomy such that motion of the subject's heart causes the probe to move against the bias force during a portion of the heart cycle. In the illustrated embodiment, the bias mechanism comprises a pulley 132 mounted on support member 70. Pulley 132 is connected by a cord 133 to one end of a tension spring 134. The opposite end of spring 134 is connected to a cord 135, wound on a pulley 136. Pulley 136 is mounted on a shaft 137, which is journalled in a side wall 138 of housing 24 and which is adjustable, by rotation of a detent knob 139 to exert an adjustable bias torque on support member 70. The bias urges the probe 20 or 20A toward the subject being monitored so as to assist in coupling the probe to the subject. Knob 139 can be releasably locked into a position corresponding to a desired bias force by means of a lock screw 140.

Figure 20:
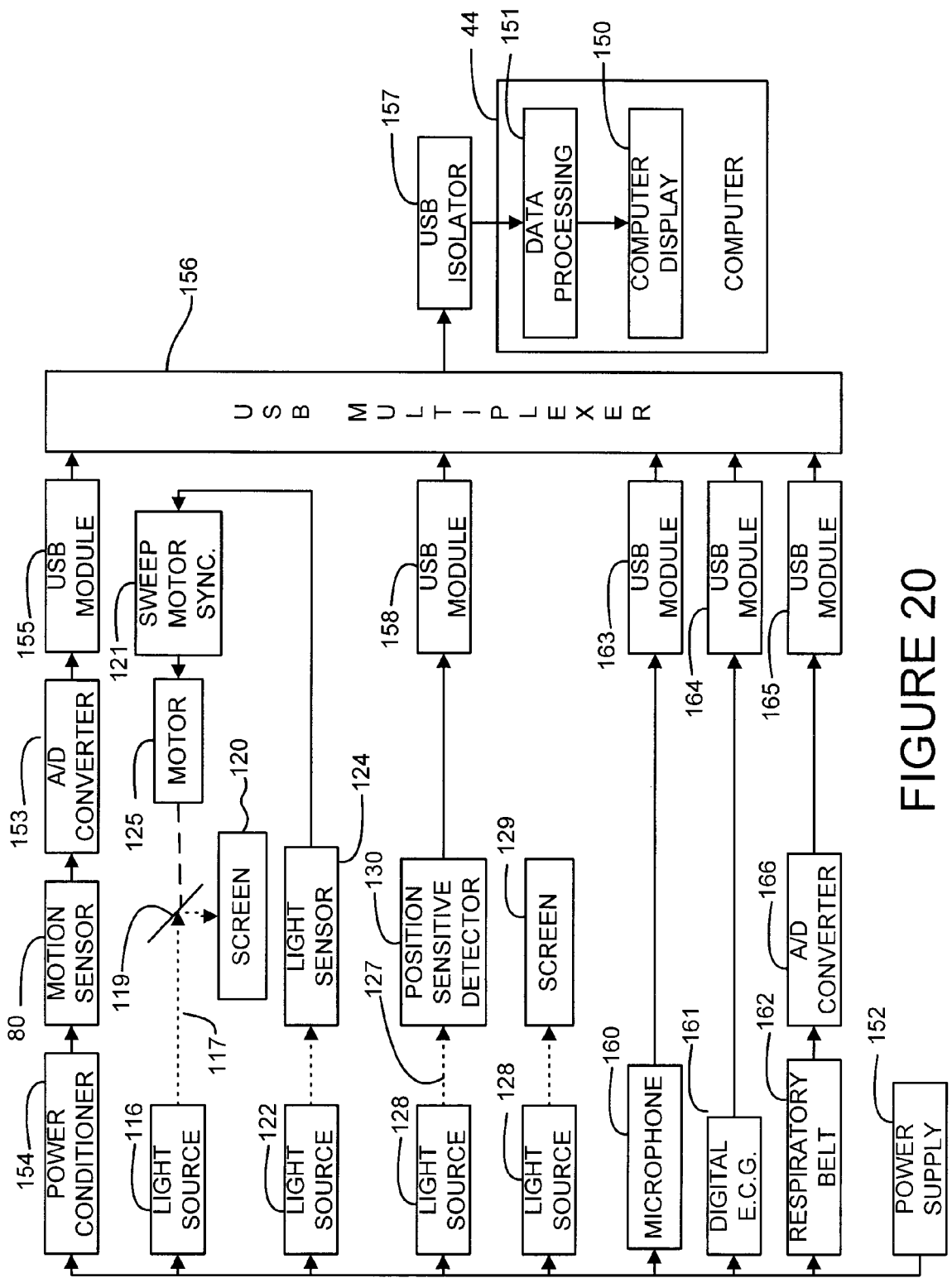
FIG. 20 is a block diagram of the components of an example heart motion detection apparatus; and, FIG. 21 is an example heart motion waveform of a type that may be produced by applying methods and apparatus according to some of the embodiments disclosed herein.

FIG. 20 diagrammatically illustrates the processing of the data obtained by apparatus 10. Signals from motion sensor 80 are processed by computer system 44. Waveforms or other information of diagnostic interest may be derived from the signals by a data processor 151 executing suitable data processing algorithms and displayed on a computer display 150, which may be the display of computer 44 (FIG. 1). Display 150 may, for example, display displacement and acceleration waveforms as well as graphical and/or textual indications of the amplitudes of one or both of the acceleration and displacement waveforms. Other waveforms, such as ECG waveforms may also be displayed on display 150.

A power supply 152 is connected to supply electrical power to the components of apparatus 10. In some embodiments, power supply 152 is part of computer system 44. Power supply 152 supplies power through a power conditioner 154 to motion sensor 80. The output signal from motion sensor 80 is conditioned, as desired by suitable analog signal conditioning and amplification circuits and digitized at an analog-to-digital converter (ADC) 153. The digitized signal is carried to computer 44 by a suitable data communication channel such as a USB bus. In the illustrated embodiment, the signal is carried to computer 44 by way of USB module 155, a USB multiplexor 156 and a USB isolator 157.

Light sources 116, 122 and 128 are also powered by power supply 152. The deflection of beam 127 as measured by position sensing diode array 130 may be delivered to computer 44 by way of the data channel (through USB module 158) as a displacement waveform that directly indicates the angular displacement of support member 70.

Because light source 128 may be employed with a screen 129 or with a position sensing diode array 130, it is shown twice in FIG. 20.

Housing 24 has sockets 159 for connecting accessories such as a digital microphone 160, a digital ECG apparatus 161 and a digital respiratory belt 162. These accessories are diagrammatically illustrated in FIG. 20 and are associated in known manner with the subject to be monitored when apparatus 10 is in use.

FIG. 20 shows that signals from digital microphone 160, digital ECG apparatus 161 and digital respiratory belt 162 are connected to respective USB modules 163, 164 and 165 respectively. USB modules, 163, 164 and 165 deliver data through USB multiplex system 156 and USB isolator 157 to computer 44. In the illustrated embodiment, respiratory belt 162 produces an analog output signal. The output of respiratory belt is concerted to a stream of digital values by analog-to-digital converter 166.

FIG. 21 shows example heart motion wave forms. Curve 202 (solid line) is an example of motion detected at a subject's aortic arch. Curve 204 (dashed line) is an example of motion detected at a subject's thyroid cartilage. In FIG. 21, the amplitudes of both waveforms have been normalized by setting the maximum and minimum amplitudes of each waveform to +1 and −1 respectively.

In apparatus according to some embodiments of the invention, various cardiac parameters may be simultaneously recorded. For example, apparatus according to the invention may record and display any or all of:
acceleration,
displacement,
ECG,
phonocardiogram, and
respiration.

The example apparatus described herein may be varied in many ways. The following are some non-limiting examples of ways in which the apparatus may be varied. Any of a wide variety of sensors may be used to measure displacement of support member 70. For example:
a miniature linear potentiometer may be coupled to support member 62;

optical methods (including those described above) may be used;

an output of accelerometer 80 may be integrated;

a rotary encoder may be connected to measure the angular position of support member 70;

a capacitive sensor may be provided; and, the like.

Any of a wide variety of bias mechanisms may be provided to bias probe 20 or 20A against the subject's anatomy. For example:

an electromagnetic mechanism may be provided to apply a torque to lever 50;

a torsion spring may be connected between support member 70 and a suitable anchor point;

a magnetic mechanism may be provided to apply a torque to lever 50;

an electromagnetic mechanism may be provided to apply a force to probe 20;

a spring may be connected between probe 20 and a suitable anchor point to apply a force to probe 20;

a magnetic mechanism may be provided to apply a force to probe 20; or, the like.

Any of a wide variety of mechanisms may be provided to provide mechanical amplification of the motion of probe 20 or 20A. For example:

the probe may cause motion of a cam that, in turn, causes the amplified motion detected by the motion sensor.

the probe may move links of a multi-link mechanical linkage that causes the amplified motion detected by the motion sensor.

other types of motion-amplifying mechanical linkage may be provided to connect the probe to the motion sensor.

Data from apparatus 10 may be processed and displayed in a wide variety of alternative ways. The data processing may be controlled by software executing on computer system 44. For example:

Any combination of waveforms detected by apparatus 10 may be displayed together. This allows a clinician, researcher, or other observer to observe correlations between features of the waveforms.

Correlations may be computed between different waveforms.

Average displacements, velocities and/or accelerations may be computed for one or more selected windows in a wave form. The averages may be computed for waveforms for a series of heartbeats.

Artefacts due to breathing or relative motion between the subject and apparatus 10 may be identified and removed or marked.

Data may be displayed in real time, stored for future display and/or processing, or both.

Data processing apparatus, such as computer system 44 may be integrated within housing 24 if desired.

Acceleration waveforms can be difficult to interpret. In some embodiments of the invention, acceleration and displacement waveforms are displayed simultaneously. The displacement waveform is useful for interpreting the acceleration waveform since the direction of the acceleration, especially during the isovolumic phase, can be determined from the displacement. Knowing the direction of acceleration can assist in the diagnosis of paradoxical left ventricular motion, which is an indicator of cardiac muscle damage. Paradoxical left ventricular motion is indicated when the direction of acceleration is opposite to normal during parts of the heart cycle. The shapes and magnitudes of the displacement and acceleration waveforms can indicate the degree of elasticity of the left ventricular wall.

Apparatus 10, as described above, enables waveforms of cardiac motions to be obtained non-invasively from two different body sites, e.g. from the aortic arch and the trachea. Another signal, such as an ECG or a recording of heart sounds may be acquired simultaneously with each of the heart motion waveforms. The heart motion waveforms may be combined into a single resultant waveform, using the ECG or other signal as a phase marker, thereby providing more detailed diagnostic information than can be obtained from a single body site. In the alternative, signal processing techniques may be used to synchronize two (or more) heart motion waveforms. The two waveforms can be independently analyzed and compared with one another and also with the resultant waveform. A resultant waveform may be obtained, for example, by adding or subtracting two heart motion waveforms. Preferably the heart motion waveforms are normalized in both amplitude and time before they are combined. Apparatus 10 or computer 44 may display one or more of the waveforms.

Normalizing a heart motion waveform for display or analysis may comprise amplifying and/or applying an offset to the waveform so that maximae and minimae of the waveform have predetermined values such as +1 and −1. Other suitable normalization methods may be used in the alternative. For example, the waveform may be offset so that its average has a desired value, such as zero, and then amplified such that its maximae (or minimae) have a desired value, for example +1 (or −1).

In some embodiments, an ECG waveform is displayed together with a waveform representing heart motion. The QRS complex in the ECG waveform typically occurs shortly prior to the commencement of the isovolumic phase of the heart cycle. Useful diagnostic information may be obtained by considering a heart motion waveform together with an ECG waveform.

Apparatus 10 may be applied to measure the ejection fraction in a very cost effective manner by constructing a nomogram. This may be done by using apparatus 10 to obtain values for the amplitudes of heart motion during each of the isovolumic and ejection phases of the heart cycle for test subjects having a range of known ejection fractions. In resting healthy adults, the ejection fraction is known to be approximately 67%. The ejection fraction can be altered by exercising a subject. Also, subjects having heart abnormalities may have rejection fractions at rest that differ significantly from 67%. The ejection fraction of test subjects may be measured by taking echocardiographs. The test subjects preferably include healthy subjects as well as subjects having ejection fractions in the range of 17% to 57% as determined by echocardiographic methods. Errors can be avoided by not using data when there are indications of valve abnormalities. Valve abnormalities are indicated when high motion amplitude values of the isovolumetric phase do not occur with high motion amplitude values in the ejection phase or vice versa.

Heart motion data taken by measuring motions of the aortic arch, thyroid cartilage, or both sites may be used to construct the nomogram.

Apparatus 10 is also used to measure values for the amplitudes of heart motion for the test subjects during each of the isovolumic and ejection phases. The nomogram can be constructed so that the amplitudes of the heart motions in the isovolumic and ejection phases indicate the ejection fraction. As an equivalent to a nomogram, a mathematical formula that predicts the ejection fraction based at least upon the amplitudes of the heart motions in the isovolumic and ejection phases may be fitted to the data from the test subjects. Once the nomogram or mathematical formula has been constructed, the ejection fraction of a subject can be obtained by measuring the amplitudes of the heart motion during the isovolumic and ejection phases of a subject's heart cycle and using these values as inputs to the nomogram or mathematical formula.

It can be appreciated that apparatus as described herein may be constructed to provide two or more different sensors that may be used simultaneously to sense heart motions. The different sensors may include acceleration and displacement sensors. A variety of sensors, including optical types, may be utilized. The strong coupling between probe 20 or 20A that is facilitated by the bias mechanism enables mechanical and optical amplification, thereby reducing or avoiding any need for high gain electronic amplification and the electrical noise that can be introduced by high gain electronic amplification. Apparatus as described herein can enable the recording of very small but clinically significant motions of the heart, e.g. motions due to the passive inflow of blood into the ventricles.

A simplified apparatus 10 may be used for screening for heart issues. In some embodiments, the screening apparatus may lack accelerometer 80 and its associated electronics. In such a device, a light beam, such as beam 127 is deflected in response to heart motion and information regarding the subject's heart can be obtained by observing deflections of the light beam on a screen, electronic display, or the like.

Where a component (e.g. a computer, software, processor, assembly, device, circuit, coupling etc.) is referred to above, unless otherwise indicated, reference to that component (including a reference to a "means") should be interpreted as including as equivalents of that component any component which performs the function of the described component (i.e., that is functionally equivalent), including components which are not structurally equivalent to the disclosed structure which performs the function in the illustrated exemplary embodiments of the invention.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

What is claimed is:

1. Apparatus for non-invasively monitoring motions of a subject's heart, the apparatus comprising:
    a probe adapted to bear against an anatomical structure of the subject by way of the subject's skin, the anatomical structure being an anatomical structure that is moved in a first direction by motions of the subject's heart mass to transmit the motions of the subject's heart mass to the probe when the probe is bearing against the anatomical structure thereby causing movement of the probe in the first direction;
    a movement sensor connected to sense motions of the probe in the first direction;
    an adjustable bias mechanism coupled to bias the probe in the first direction against the anatomical structure with a bias force; and
    a control operable by a user to continuously vary a magnitude of the bias force applied to the probe by the bias mechanism.

2. Apparatus according to claim 1 comprising an adjustable support mechanism that is external to the subject and operable to hold the probe in place against the anatomical structure.

3. Apparatus according to claim 1 wherein the movement sensor comprises an accelerometer.

4. Apparatus according to claim 3 comprising an acceleration display connected to display an output of the accelerometer.

5. Apparatus according to claim 1, wherein the probe is at one end of a lever mounted to pivot about a pivot axis, the movement sensor is provided on the lever, and the pivot axis is between said one end and the movement sensor.

6. Apparatus according to claim 5 wherein the lever is pivotally coupled to a member that is supported by a support mechanism relative to a base on which the apparatus is mounted.

7. Apparatus according to claim 1 comprising an electrocardiograph for generating an electrocardiogram waveform and a memory for storing the electrocardiogram waveform and a waveform generated from an output of the movement sensor.

8. Apparatus for non-invasively monitoring motions of a subject's heart, the apparatus comprising:
    a probe adapted to bear against an anatomical structure of the subject by way of the subject's skin, the probe moveable in a first direction in response to heart motions of the subject;
    a movement sensor connected to sense motions of the probe in the first direction;
    a bias mechanism coupled to bias the probe in the first direction against the anatomical structure with a bias force; and
    a mechanical motion amplifier coupled between the probe and the motion sensor wherein the mechanical motion amplifier is adjustable to adjust an amount of mechanical amplification at the motion sensor of the motion of the probe.

9. Apparatus according to claim 8 wherein the mechanical motion amplifier comprises a lever mounted to pivot about a pivot axis.

10. Apparatus for non-invasively monitoring motions of a subject's heart, the apparatus comprising:
    a probe adapted to bear against an anatomical structure of the subject by way of the subject's skin, the probe moveable in a first direction in response to heart motions of the subject;
    a movement sensor connected to sense motions of the probe in the first direction;
    an adjustable bias mechanism coupled to bias the probe in the first direction against the anatomical structure with a bias force;
    a user-adjustable control operable to set a desired magnitude of the bias force applied to the probe by the bias mechanism;
    a mechanical motion amplifier coupled between the probe and the motion sensor;
    wherein the mechanical motion amplifier comprises a lever mounted to pivot about a pivot axis; and
    wherein the bias mechanism comprises a spring coupled to impart a torque to the lever.

11. Apparatus for non-invasively monitoring motions of a subject's heart, the apparatus comprising:
    a probe adapted to bear against an anatomical structure of the subject by way of the subject's skin, the probe moveable in a first direction in response to heart motions of the subject;
    a movement sensor connected to sense motions of the probe in the first direction;

an adjustable bias mechanism coupled to bias the probe in the first direction against the anatomical structure with a bias force;

a user-adjustable control operable to set a desired magnitude of the bias force applied to the probe by the bias mechanism;

comprising a mechanical motion amplifier coupled between the probe and the motion sensor;

wherein the mechanical motion amplifier comprises a lever mounted to pivot about a pivot axis; and comprising means for applying a torque to the lever to bias the probe against the subject.

12. Apparatus for non-invasively monitoring motions of a subject's heart, the apparatus comprising:

a probe adapted to bear against an anatomical structure of the subject by way of the subject's skin, the probe moveable in a first direction in response to heart motions of the subject;

a movement sensor connected to sense motions of the probe in the first direction;

a bias mechanism coupled to bias the probe in the first direction against the anatomical structure; and a user-adjustable control operable to set a bias force applied to the probe by the bias mechanism;

wherein the probe is at one end of a lever mounted to pivot about a pivot axis, the movement sensor is provided on the lever, and the pivot axis is between said one end and the movement sensor, and wherein the lever is pivotally mounted to the apparatus by spaced-apart electrically-conducting pivots that are electrically insulated from one another and the motion sensor is coupled to signal processing circuits by way of an electrical connection extending through the pivots.

13. Apparatus according to claim 12, wherein the movement sensor is movable along the lever for varying an amount of mechanical amplification of the motion of the probe.

14. Apparatus for non-invasively monitoring motions of a subject's heart, the apparatus comprising:

a probe adapted to bear against an anatomical structure of the subject by way of the subject's skin, the probe moveable in a first direction in response to heart motions of the subject;

a movement sensor connected to sense motions of the probe in the first direction;

an adjustable bias mechanism coupled to bias the probe in the first direction against the anatomical structure with a bias force; and a user-adjustable control operable to set a desired magnitude of the bias force applied to the probe by the bias mechanism;

wherein the probe comprises a thin elongated member adapted for coupling the apparatus to the aortic arch of the subject.

15. Apparatus according to claim 14, wherein a free end of the probe protrudes through an open end of a shield.

16. Apparatus according to claim 15 wherein the free end of the probe projects through a ring defined by the shield, wherein the ring is spaced-apart radially from the free end of the probe.

17. Apparatus for non-invasively monitoring motions of a subject's heart, the apparatus comprising:

a probe adapted to bear against an anatomical structure of the subject, the probe moveable in a first direction in response to heart motions of the subject, the probe comprising a thin elongated member adapted for coupling the apparatus to the aortic arch of the subject;

a movement sensor connected to sense motions of the probe in the first direction;

a bias mechanism coupled to bias the probe in the first direction against the anatomical structure; and a pair of spaced apart lobes supported by a shield on opposed sides of the free end of the probe;

wherein a free end of the probe protrudes through an open end of the shield.

18. Apparatus for non-invasively monitoring motions of a subject's heart, the apparatus comprising:

a probe, adapted to bear against an anatomical structure of the subject by way of the subject's skin, the probe moveable in a first direction in response to heart motions of the subject, wherein the probe comprises a thin elongated member adapted for coupling the apparatus to the aortic arch of the subject;

a movement sensor connected to sense motions of the probe in the first direction;

a bias mechanism coupled to bias the probe in the first direction against the anatomical structure;

a user-adjustable control operable to set a bias force applied to the probe by the bias; and a jaw and head support engageable with the subject's jaw and head for supporting the subject's jaw and head while the probe is coupled to register movements of the subject's aortic arch.

19. Apparatus for non-invasively monitoring motions of a subject's heart, the apparatus comprising:

a probe adapted to bear against an anatomical structure of the subject by way of the subject's skin, the probe moveable in a first direction in response to heart motions of the subject;

a movement sensor connected to sense motions of the probe in the first direction;

an adjustable bias mechanism coupled to bias the probe in the first direction against the anatomical structure with a bias force; and a user-adjustable control operable to set a desired magnitude of the bias force applied to the probe by the bias mechanism;

wherein the probe comprises a projection configured to engage a thyroid notch of the subject.

20. Apparatus for non-invasively monitoring motions of a subject's heart, the apparatus comprising:

a probe adapted to bear against an anatomical structure of the subject by way of the subject's skin, the probe moveable in a first direction in response to heart motions of the subject, wherein the probe comprises a projection engageable on a thyroid notch of the subject and in cross section, the projection has side faces that are inclined relative to one another and are joined by a rounded lower surface;

a movement sensor connected to sense motions of the probe in the first direction;

a bias mechanism coupled to bias the probe in the first direction against the anatomical structure; and a user-adjustable control operable to set a bias force applied to the probe by the bias mechanism.

21. Apparatus according to claim 20 comprising a pair of resilient arms, one of the resilient arms disposed on each side of the projection.

22. Apparatus for non-invasively monitoring motions of a subject's heart, the apparatus comprising:
- a probe adapted to bear against an anatomical structure of the subject by way of the subject's skin, the probe moveable in a first direction in response to heart motions of the subject;
- a movement sensor connected to sense motions of the probe in the first direction;
- a bias mechanism coupled to bias the probe in the first direction against the anatomical structure;
- a user-adjustable control operable to set a bias force applied to the probe by the bias mechanism; and
- a displacement display indicative of a displacement of the probe and an optical motion amplifier between the probe and the displacement display.

23. Apparatus according to claim 22 wherein the optical motion amplifier comprises a mirror mounted on the support member, and a light source located to direct a beam of light onto the mirror to yield a reflected beam, the displacement display being in a path of the reflected beam.

24. Apparatus according to claim 22, comprising a table for supporting the subject, the table tiltable to place the subject into a head-down posture.

25. Apparatus for non-invasively monitoring motions of a subject's heart, the apparatus comprising:
- a probe adapted to bear against an anatomical structure of the subject by way of the subject's skin, the probe moveable in a first direction in response to heart motions of the subject;
- a movement sensor connected to sense motions of the probe in the first direction;
- a bias mechanism coupled to bias the probe in the first direction against the anatomical structure;
- a user-adjustable control operable to set a bias force, applied to the probe by the bias mechanism; and
- a first means for displaying an amplitude of the heart motion and a second means for displaying a displacement of the heart motion.

26. Apparatus for non-invasively monitoring motions of a subject's heart, the apparatus comprising:
- a probe adapted to bear against an anatomical structure of the subject, the probe moveable in a first direction in response to heart motions of the subject;
- a movement sensor connected to sense motions of the probe in the first direction;
- a bias mechanism coupled to bias the probe in the first direction against the anatomical structure
- an electrocardiograph for generating an electrocardiogram waveform and a memory for storing the electrocardiogram waveform and a waveform generated from an output of the movement sensor; and
- means for combining first and second waveforms each generated from the output of the movement sensor to yield a combined motion waveform.

27. A method for non-invasively monitoring motions of a subject's heart, the method comprising:
- applying a bias force to bias a probe against an anatomical structure of the subject in a first direction;
- allowing the probe to move against the bias force in response to motions of the subject's heart; and,
- measuring motions of the probe;
- wherein:
- measuring motions of the probe comprises mechanically amplifying the motions of the probe to yield amplified motions and measuring the amplified motions; and
- mechanically amplifying the motions of the probe comprises allowing the probe to act on a lever at a first distance from a pivot axis of the lever and measuring motion of the lever at a second distance from the pivot axis that is greater than the first distance.

28. A method according to claim 27 wherein measuring motions of the probe comprises measuring an output of an accelerometer that experiences the amplified motions.

29. A method according to claim 27 wherein applying the bias force comprises applying a torque to the lever, the torque tending to rotate the lever about the pivot axis.

30. A method according to claim 27 wherein the anatomical structure comprises an aortic arch of the subject.

31. A method according to claim 27 wherein the anatomical structure comprises a thyroid cartilage of the subject.

32. A method according to claim 27 comprising acquiring an electrocardiogram while measuring the motions of the probe.

33. A method according to claim 32 comprising displaying both a waveform representing the motions of the probe and an electrocardiogram waveform on a display.

34. A method according to claim 33 comprising storing electrocardiogram data and data representing the motions of the probe in a memory.

35. A method according to claim 27 comprising, prior to measuring motions of the probe, performing a calibration procedure comprising:
- imparting a known motion to the probe; and,
- adjusting a mechanical amplifier until an output signal of a motion sensor coupled to the probe by the mechanical amplifier has a desired value.

36. A method according to claim 35 wherein the mechanical amplifier comprises a lever and adjusting the mechanical amplifier comprises moving the motion sensor along the lever.

37. A method for non-invasively monitoring motions of a subject's heart, the method comprising:
- providing apparatus comprising a probe and a biasing mechanism;
- applying, using the biasing mechanism, a bias force to bias the probe in a first direction against an anatomical structure of the subject by way of the subject's skin;
- setting a magnitude of the bias force;
- allowing the probe to move against the bias force in response to motions of the subject's heart; and,
- measuring motions of the probe;
- wherein the anatomical structure comprises an aortic arch of the subject, the method comprising inserting the probe behind the right side of the subject's manubrium, substantially parallel to the main axis of the heart, to a depth greater than 1.5 inches.

38. A method for non-invasively monitoring motions of a subject's heart, the method comprising:
- applying a bias force to bias a probe in a first direction against an anatomical structure of the subject by way of the subject's skin;
- setting a magnitude of the bias force;
- allowing forces resulting from changes in momentum of the subject's heart mass to be transferred directly to the probe by way of the anatomical structure such that the probe is caused to move against the bias force in direct response to the motions of the subject's heart mass; and,
- measuring motions of the probe and maintaining the subject in a head-down posture while measuring the motions of the probe.

39. A method for non-invasively monitoring motions of a subject's heart, the method comprising:
- applying a bias force to bias a probe against an anatomical structure of the subject in a first direction;
- allowing the probe to move against the bias force in response to motions of the subject's heart; and,
- measuring motions of the probe
- wherein the anatomical feature constitutes a first anatomical feature, the method comprises storing a record of the motions of the probe as first data and the method further comprises obtaining second data by:
- applying a bias force to bias a probe against a second anatomical structure of the subject;
- allowing the probe to move against the bias force in response to motions of the subject's heart; and
- measuring motions of the probe; and
- combining the first data and the second data to yield a combined waveform.

40. A method according to claim 39 wherein combining the first data and the second data comprises adding the first and second data.

41. A method according to claim 39 wherein combining the first data and the second data comprises subtracting the first and second data.

42. A method according to claim 39 wherein each of the first and second data includes an ECG waveform and combining the first and second data comprises synchronizing the first and second data based on the ECG waveforms.

43. A method for non-invasively monitoring motions of a subject's heart, the method comprising:
- providing apparatus comprising a probe and a biasing mechanism;
- applying, using the biasing mechanism, a bias force to bias the probe in a first direction against an anatomical structure of the subject by way of the subject's skin;
- setting a magnitude of the bias force;
- allowing the probe to move against the bias force in response to motions of the subject's heart; and,
- measuring motions of the probe;
- wherein the anatomical structure comprises an aortic arch of the subject and the method comprises advancing the probe into proximity of the subject's aortic arch while maintaining the subject in a posture wherein the subject's head is rotated to the subject's right and the subject is inhaling.

44. A method for non-invasively monitoring motions of a subject's heart, the method comprising:
- providing apparatus comprising a probe and a biasing mechanism;
- applying, using the biasing mechanism, a bias force to bias the probe in a first direction against an anatomical structure of the subject by way of the subject's skin;
- setting a magnitude of the bias force;
- allowing the probe to move against the bias force in response to motions of the subject's heart; and,
- measuring motions of the probe; and
- determining a lung resistance of the subject by monitoring displacements of the probe corresponding to breaths of the subject.

45. Apparatus for non-invasively monitoring motions of a subject's heart, the apparatus comprising:
- a probe adapted to bear against an anatomical structure of the subject by way of the subject's skin, the probe moveable in a first direction in response to heart motions of the subject;
- a movement sensor connected to sense motions of the probe in the first direction;
- a bias mechanism coupled to bias the probe in the first direction against the anatomical structure with a bias force; and
- a mechanical motion amplifier coupled between the probe and the motion sensor wherein the mechanical motion amplifier is adjustable to adjust an amount of mechanical amplification at the motion sensor of the motion of the probe and the mechanical motion amplifier comprises a lever mounted to pivot about a pivot axis;
- wherein the movement sensor is movable along the lever for varying an amount of mechanical amplification of the motion of the probe.

46. A method for non-invasively obtaining a waveform representing motions of a subject's heart, the method comprising:
- biasing a probe into contact with an anatomical structure of the subject, the anatomical structure being a structure that moves in a first direction in direct response to motions of the subject's heart mass such that the motions of the subject's heart mass are transmitted to the probes by the anatomical structure;
- mechanically amplifying motions of the probe to yield amplified motion;
- applying the amplified motion to a motion sensor;
- at the motion sensor, sensing the amplified motion to yield an electrical signal;
- digitizing the electrical signal to yield a digitized electrical signal; and,
- processing the digitized electrical signal to yield a waveform representing the motions of the subject's heart mass.

* * * * *